(12) United States Patent
Bridge et al.

(10) Patent No.: US 8,236,533 B2
(45) Date of Patent: Aug. 7, 2012

(54) PROCESS FOR THE PRODUCTION OF γ-GLUTAMYLCYSTEINE

(75) Inventors: Wallace John Bridge, Sydney (AU); Martin Hani Zarka, Merewether (AU)

(73) Assignee: NewSouth Innovations PTY Limited, Sydney (AU)

( * ) Notice: Subject to any disclaimer, the term of this patent is extended or adjusted under 35 U.S.C. 154(b) by 916 days.

(21) Appl. No.: 11/887,667

(22) PCT Filed: Mar. 31, 2006

(86) PCT No.: PCT/AU2006/000437
§ 371 (c)(1),
(2), (4) Date: Aug. 7, 2008

(87) PCT Pub. No.: WO2006/102722
PCT Pub. Date: Oct. 5, 2006

(65) Prior Publication Data
US 2009/0136993 A1    May 28, 2009

(30) Foreign Application Priority Data

Mar. 31, 2005  (AU) ................................ 2005901571

(51) Int. Cl.
*C12P 7/62* (2006.01)
(52) U.S. Cl. ........ 435/135; 435/195; 435/196; 435/197; 435/198; 435/228
(58) Field of Classification Search .................. 435/135, 435/196, 197, 198, 228, 195
See application file for complete search history.

(56) References Cited

U.S. PATENT DOCUMENTS

| 3,045,026 | A | 7/1962 | Eisenbraun |
| 3,770,807 | A | 11/1973 | Sumikawa et al. |
| 5,106,463 | A | 4/1992 | Genders et al. |
| 6,495,170 | B1 | 12/2002 | Smit et al. |

FOREIGN PATENT DOCUMENTS

| CN | 1163902 | 11/1997 |
| JP | 55077888 A | 6/1980 |
| WO | WO 92/00320 | 1/1992 |

OTHER PUBLICATIONS

Griffith et al., "Formation of γ-glutamylcyst(e)ine in vivo is catalyzed by γ-glutamyl transpeptidase," *Proc. Natl. Acad. Sci. USA*, 78:2777-2781 (1981).
Tate et al., "Interaction of γ-Glutamyl Transpeptidase with Amino Acids, Dipeptides, and Derivatives and Analogs of Glutathione," *The Journal of Biological Chemistry*, 249:7593-7602 (1974).
Abe et al., *J Org Chem* 39(2):253-255, 1974.
Batistaviera et al., *Applied Biochem & Biotechnol* 44(1):1-14, 1994.
Belew & Porath, *J Chromatogr* 516:333-354, 1990.
Brois et al., *J Amer Chem Soc* 92(26):7629, 1970.
Budy et al., *Anal Biochem* 291(2):303-305, 2001.
Choi et al., *J Org Chem* 60(11):3266-3267, 1995.
Clarke, *J Biol Chem* 97:235, 1932.
Do, *Tetrahedron Lett* 38:3383-3384, 1997.
Eager et al., *Photochem & Photobiol* 2(1):25-37, 1963.
Galzigna et al., *Enzyme & Protein* 48(2):98-104, 1994.
Gotoh et al., *Biochem Engineering J* 19:165-170, 2004.
Guttmann, *Helvetica Chimica Acta* 49:83-96, 1965.
Jocelyn, *Methods of Enzymol* 143:246-256, 1987.
Kudryavtseva et al., *Uspekhi Khimii* 67(7):611-630, 1998.
Lichtenstein, *J Amer Chem Soc* 64:1021-1022, 1942.
Martin-Orue, *J Membrane Sci* 142:225-233, 1998.
Maugras et al., *Int J Peptide & Protein Res* 45(2):152-156, 1995.
Milkowski et al., *Org Syntheses* 6:5-8, 1988.
Moore et al., *J Biol Chem* 262:16771-16777, 1987.
Nagasawa et al. *Organic Preparations and Procedures International (Briefs)*, 28(2):237-241, 1996.
Peterson, *Anaytical Biochem* 83:346-356, 1977.
Ralph et al., *J Electroanal Chem* 462:97-110, 1999.
Rietman et al., *Synth Commun* 24(9):1323-1332, 1994.
Savige et al., *Tetrahedron Lett* 43-44:32889-3293, 1964.
Schoberl et al., *Annalen Der Chemie-Justus Liebig* 617(1-3):71-78, 1958.
Singh et al., *J Org Chem* 56(24):6931-6933, 1991.
Szewczuk & Baranowski, *Biochimische Zeitschrift* 338(338):317-329, 1963.
Stapleton et al., *Australian J Chem* 15(3):570, 1962.
Uotila et al., *Biochem* 12:3938-3943, 1973.
Walti et al., *J Chem Soc C-Organic* 12:2326, 1971.

*Primary Examiner* — Susan Hanley
(74) *Attorney, Agent, or Firm* — Jones Day

(57) ABSTRACT

The present invention relates to a process for preparing a compound comprising an α,γ amide linkage between a cysteine moiety and a glutamic acid moiety, such as γ-glutamylcysteine or a γ-glutamylcysteine derivative, the process comprising providing a cysteine derivative, a γ-glutamyl donor and an enzyme capable of transferring the γ-glutamyl group to said cysteine derivative in a reaction environment promoting transfer of the γ-glutamyl group to said cysteine derivative. The invention also relates to compounds comprising an α,γ amide linkage between a cysteine moiety and a glutamic acid moiety, such as γ-glutamylcysteine or a γ-glutamylcysteine derivative, when obtained by processes of the invention, and uses thereof.

34 Claims, 10 Drawing Sheets

PROCESS FOR THE PRODUCTION OF γ-GLUTAMYLCYSTEINE

FIELD OF THE INVENTION

The present invention relates to enzymic processes for the production of γ-glutamylcysteine, and γ-glutamylcysteine produced by such processes, and its uses.

BACKGROUND TO THE INVENTION

All aerobic organisms use molecular oxygen for respiration and oxidation of nutrients for energy. During the reduction of molecular oxygen to water, reactive oxygen species, also know as free radicals, are generated. They are extremely reactive and can attack and damage almost all cellular components including DNA, proteins and lipids. Oxidative to stress induced by these reactive oxygen species has been implicated in many diverse degenerative diseases, including aging, arthritis, arteriosclerosis, AIDS, cancer, cataracts, hepatitis, myocardial infarction, Alzheimer's disease and stroke. To combat oxidative stress, cells have developed an arsenal of defense mechanisms including enzymes and antioxidants such as ascorbate, α-tocopherol, uric acid, β-carotene and glutathione. As the major cellular antioxidant, glutathione's metabolism and modulation is vital in the protection against oxidative stress.

Glutathione (GSH) is a tripeptide of γ-glutamic acid, cysteine and glycine, and is the most biologically abundant low-molecular weight intracellular thiol, and by way of the reducing power of its free sulphydryl (—SH), it plays a key role in many cellular processes. These include protection of cells against oxidative stress, xenobiotics and radiation. GSH is synthesized intracellularly from its constituent amino acids by the consecutive action of γ-glutamylcysteine synthetase (γ-GCS) and GSH synthetase (GS) with both reactions consuming ATP:

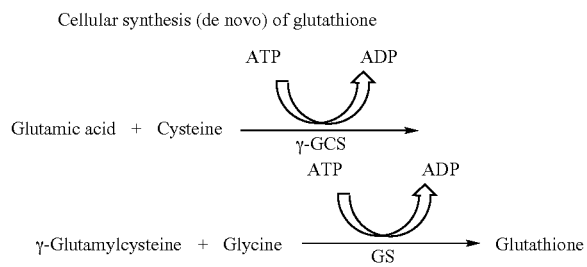

Cellular synthesis (de novo) of glutathione

Lowered cellular and tissue levels of GSH is being implicated in the pathogenesis of an ever growing list of diseases and degenerative conditions, especially those associated with free radical injury. Restoration of cellular GSH levels in the treatment of a number of these medical conditions has proven to be beneficial.

Administration of GSH is considered ineffective in increasing cellular GSH as it is not effectively transported into cells and is degraded to its amino acids extracellularly. Administration of cysteine, the limiting amino acid in GSH synthesis, is also considered ineffective as it rapidly oxidizes to poorly soluble cystine and is reportedly toxic. Strategies for increasing GSH levels have focused mainly on cysteine delivery compounds such as N-acetylcysteine and 2-oxothiazalidine-4-carboxylate. Elevating GSH levels by using cysteine prodrugs is of limited use due to the feedback inhibition by GSH on the first synthetic enzyme γ-GCS. The second enzyme, GS, is not subject to feedback inhibition and its substrate, GGC, is usually the limiting substrate in GSH synthesis. γ-Glutamylcysteine (GGC) is the most immediate precursor to GSH, and GGC is normally present at lower levels than cysteine. Many cell types have the ability to transport exogenous GGC across the cell membrane and GGC has been shown to have clinical potential to elevate cellular GSH levels.

γ-Glutamylcysteine occurs naturally in bovine milk and is especially rich in the whey fraction where it occurs linked via a disulphide bond to proteins. Numerous reports have demonstrated that the consumption of whey proteins increases levels of GSH. A range of whey protein isolates is commercially available and these are claimed to include GGC as the active constituent. Recent human clinical trials on muscle performance and HIV patients have confirmed the effectiveness of whey protein isolates to increase GSH levels.

Apart from the nutraceutical market for GGC, which has already been well established by whey protein isolates, other applications for GGC include the addition of GGC to foods and cosmetics as an antioxidant, and the treatment of patients that have been poisoned with heavy metals or oxidizing agents.

To date, there is no industrially suitable, cost-effective process for the production of GGC. This is due to the complex protection and de-protection chemistry required for the reactive sulphydryl of cysteine and the unconventional γ-glutamyl peptide bond.

The majority of the processes described by the scientific and patent literature on the commercial manufacture of glutathione involve the fermentation of yeast, in particular bakers yeast, *Saccharomyces cerevisiae*, which is naturally rich in GSH. However, microbial production of GGC has been found to suffer from a number of disadvantages, including: low volumetric yield; low yields on substrate; extended fermentation time (several days); complex purification procedure; generation of multiple waste streams; and high equipment capital costs.

Large-scale chemical synthesis of GSH also suffers from difficulties, due to the presence of eight functional groups on the constituent amino acids. In the case of GGC there are six functional groups. Most methods for the chemical synthesis of GSH are low yielding (<10%). The major drawback preventing the commercial success of chemical synthesis of GGC is the number of steps involved: two protection steps each for both cysteine and glutamic acid, one coupling step, and then at least another two de-protection steps. Another difficulty in the chemical synthesis of GGC is that selective protection of the α-carboxyl group of glutamic acid by esterification is complicated due to the higher reactivity of the γ-carboxyl group. The inability to use platinum catalysed hydrogenolysis (de-protection) of benzyloxycarbonyl protecting groups of the amino group of glutamate in GGC, due to the poisoning effect of the sulphur from cysteine on the platinum catalyst, is also a major disadvantage. Some minor drawbacks to chemical to synthesis of GGC include the possibility of racemization of any of the two chiral centers of GGC, which is a common problem in peptide synthesis, and the environmental safety concerns inherent in using the large volumes of toxic reagents and solvents required.

Thus, there is a need for an effective process for industrial-scale production of γ-glutamylcysteine, which does not suffer from at least one or more of the above identified disadvantages, namely low yield, costly recovery, complicated and/or expensive steps, creation of multiple waste streams; lengthy fermentation steps; and high equipment capital costs.

An object of this invention is to provide a process for producing γ-glutamylcysteine or a derivative thereof in a cost effective manner by reducing the number of reaction steps, amount of raw materials used, and the loss of starting material by the formation of by-products.

SUMMARY OF THE INVENTION

The present invention provides an efficient, relatively simple and cost-effective process for the production of γ-glutamylcysteine using enzymic synthesis.

Thus, according to an aspect of the invention, there is provided a process for preparing a compound comprising an α,γ amide linkage between a cysteine moiety and a glutamic acid moiety, comprising providing a cysteine derivative, a γ-glutamyl donor and an enzyme capable of transferring the γ-glutamyl group to said cysteine derivative in a reaction environment promoting transfer of the γ-glutamyl group to said cysteine derivative.

According to an embodiment of this embodiment, the enzyme has γ-glutamyl esterase or γ-glutamyl amidase activity, such as a γ-glutamyltranspeptidase.

According to another embodiment, the γ-glutamyl donor is a γ-ester or a γ-amide of glutamic acid.

Examples of γ-glutamyl donors for use in the methods of the present invention include γ-alkyl-, α,γ-dialkyl-, γ-p-chlorophenyl-, and γ-cyanomethyl-esters of glutamic acid.

Examples of γ-alkyl- and α,γ-dialkyl-glutamyl esters for use in the methods of the present invention include γ-methyl-, γ-ethyl-, α,γ-dimethyl, and α,γ-diethyl-esters of glutamic acid.

According to another embodiment, the cysteine derivative is water-soluble. In this aspect, examples of cysteine derivatives for use in the processes of the present invention include:
  mixed disulphides of cysteine and low molecular weight water-soluble thiols;
  S-acetylcysteine;
  S-acetamidomethylcysteine;
  S-methoxycarbonylsulphenylcysteine;
  S-sulphocysteine;
  cystine dimethyl ester; and
  cystine monomethyl ester.

Water-soluble thiols for preparation of mixed disulphides may include any appropriate low molecular weight water-soluble thiol, such as thioglycolic acid, cystamine, thioacetic acid, methanethiol or ethanethiol. An example of a suitable mixed disulphide of cysteine for use in the processes of the present invention is cysteine-mercaptoethanol mixed disulphide.

According to another embodiment, the reaction environment is aqueous. A water-miscible solvent, such as dimethylformamide, may be included in the reaction environment.

According to another embodiment of the invention, the enzyme is selected from bovine γ-glutamyltranspeptidases, such as bovine kidney or milk γ-glutamyltranspeptidases.

According to another embodiment, the enzyme is immobilised on a stationary phase, such as a resin.

According to another embodiment, the process may be a batch-wise process. Alternatively, the process may be continuous. In the latter case, the γ-glutamyl donor and the cysteine derivative may be continuously fed into an inlet of a reactor comprising immobilised enzyme and eluate comprising the product compound may be collected continuously from an outlet.

According to an embodiment of a processes of the invention, then process is for preparing a γ-glutamylcysteine derivative. Such a process may comprise providing:
  a γ-glutamyl ester;
  a cysteine derivative selected from:
    mixed disulphides of cysteine and low molecular weight water-soluble thiols;
    S-acetylcysteine;
    S-acetamidomethylcysteine;
    S-methoxycarbonylsulphenylcysteine;
    S-sulphocysteine;
    cystine dimethyl ester; and
    cystine monomethyl ester; and
  γ-glutamyltranspeptidase;
  in a reaction environment promoting transfer by the γ-glutamyltranspeptidase of the γ-glutamyl group from the γ-glutamyl ester to said cysteine derivative.

According to an embodiment of this process, the γ-glutamyl ester is selected from γ-methyl-, γ-ethyl-, α,γ-dimethyl, and α,γ-diethyl-esters of glutamic acid, and the γ-glutamyl acceptor is selected from mixed disulphides of cysteine and thioglycolic acid or cystamine or other low molecular weight water-soluble thiols.

A compound comprising an α,γ amide linkage between a cysteine moiety and a glutamic acid moiety, produced by a process as described above is also provided. The compound may be a γ-glutamylcysteine-mercaptoethanol mixed disulphide derivative.

According to another embodiment of processes of the present invention for the synthesis of a γ-glutamylcysteine derivative, the process comprises the further step of purifying the γ-glutamylcysteine derivative by electrodialysis or by ion exclusion chromatography.

The compound comprising an α,γ amide linkage between a cysteine moiety and a glutamic acid moiety may be γ-glutamylcysteine or a derivative thereof, such as a γ-glutamylcysteine-mercaptoethanol mixed disulphide derivative.

Thus, according to another embodiment of the invention, derivatizing groups are cleaved from a γ-glutamylcysteine derivative to provide γ-glutamylcysteine. According to an embodiment, the derivatizing groups are cleaved by electrochemical reduction. The γ-glutamylcysteine may then be isolated and optionally purified as the reduced or oxidised form or as a mixture of both reduced and oxidised forms.

γ-Glutamylcysteine, when produced by a process as described above, is also provided.

DETAILED DESCRIPTION OF THE INVENTION

Figure 1:
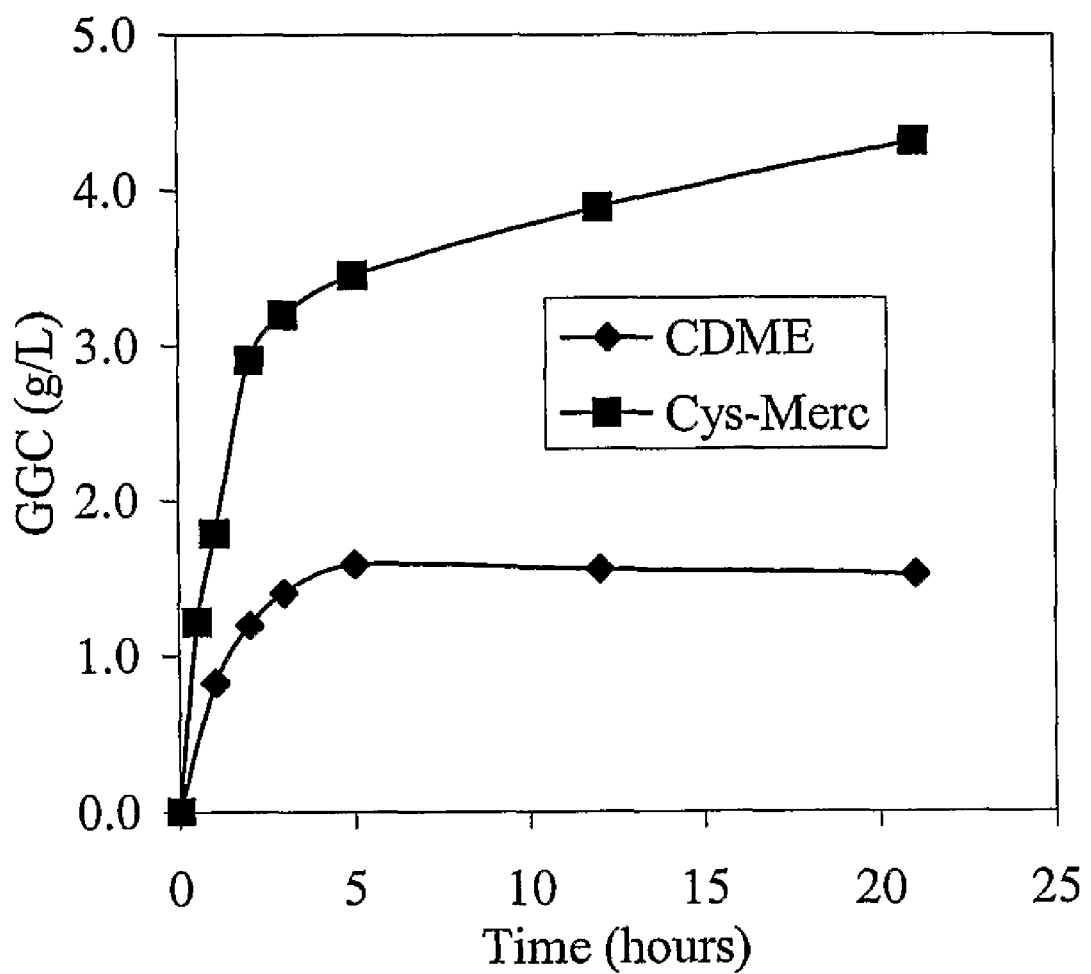
FIG. 1 illustrates the kinetics of γ-glutamyltranspeptidase (γ-GT) catalysed GGC synthesis in 50:50 water:DMF at pH 9.0, of γ-methyl ester of glutamic acid (GME, 100 mM) with cystine derivatives CDME and cysteine-mercaptoethanol mixed disulphide (100 mM).

Industrially effective processes for the production of GGC are not available. Existing non-enzymic processes typically are complex multi-step processes, require expensive equipment, involve costly recovery of the product, and involve use of toxic compounds and organic solvents and produce a variety of waste streams. Enzymic processes have also been described, but these are typically inefficient and low-yielding, often using expensive or difficult to handle starting compounds or intermediates.

As a result of the present investigations, efficient and effective processes for large/industrial-scale production of GGC have been devised. Thus, the invention provides a process for preparing a compound comprising an α,γ amide linkage between a cysteine moiety and a glutamic acid moiety, comprising a cysteine derivative, a γ-glutamyl donor and an enzyme capable of transferring the γ-glutamyl group to said cysteine derivative in a reaction environment promoting transfer of the γ-glutamyl group to said cysteine derivative.

Definitions

As used herein, the term "comprising" means "including principally, but not necessarily solely". Variations of the word "comprising", such as "comprise" and "comprises", have correspondingly similar meanings.

As used herein, the term "cysteine derivative" encompasses cysteine or its oxidised/dimerised form cystine, substituted with one or more functional groups.

An "effective amount", as referred to herein, includes a sufficient, but non-toxic amount of substance to provide the desired effect. The "effective amount" will vary from application to application (such as from use in nutraceuticals to use in pharmaceutical compositions) and even within applications (such as from subject to subject in pharmaceutical applications, and within nutraceutical forms). For any given case, an appropriate "effective amount" may be determined by one of ordinary skill in the art using only routine experimentation.

As used herein, the term "γ-glutamyl donor" encompasses any suitable compound comprising a glutamyl group which is capable of being transferred to a cysteine moiety via a γ-linkage. Such donors may be γ-amides or γ-esters, such as γ-alkyl or α,γ-dialkyl- or γ-aryl-esters of glutamic acid, which may comprise substituents selected from hydroxyl, ether, halogen, cyano, thiol, nitro, amine, or amide.

The term "isolated", where used in relation to γ-glutamyl-cysteine, indicates that the material in question has been removed from a reaction mixture, and associated impurities either reduced or eliminated. Essentially, the 'isolated' material is enriched with respect to other materials from the same source (i.e., on a molar basis it is more abundant than any other of the individual species from the given source), and preferably a substantially purified fraction is a composition wherein the 'isolated' material comprises at least about 60 percent (on a molar basis) of all molecular species present. Generally, a substantially pure composition of the material will comprise more than about 80 to 90 percent of the total of molecular species present in the composition. Most preferably, the 'isolated' material is purified to essential homogeneity (contaminant species cannot be detected in appreciable amounts).

As used herein the term "water-soluble" refers to compounds which are soluble in water at a minimum of about 2 g/L at pH 8.0-9.0, standard temperature and pressure (25° C. and 1 atmosphere of pressure).

Unless otherwise stated, where reference is made to the amino acids glutamic acid and cysteine (or cystine), the L-isomer of these compounds is implied.

Enzymes for Use in the Processes of the Invention

Any enzyme capable of transferring a γ-glutamyl group from a γ-glutamyl donor to a cysteine derivative is contemplated by the present invention. Although the normal biological function of a number of enzymes is to remove amino acids from proteins or peptides, or to hydrolyse proteins or peptides, these reactions are often reversible under appropriate conditions. Accordingly, enzymes for which the thermodynamically favourable reaction is removal of γ-glutamyl groups from compounds are contemplated within the scope of the present invention along with those for which the thermodynamically favourable reaction is addition or transfer of γ-glutamyl groups to compounds. Accordingly, enzymes which are contemplated for use in processes of the invention include transpeptidases such as γ-glutamyltranspeptidases (E.C. 2.3.2.2), and hydrolases having esterase activity such as γ-glutamylhydrolases (E.C. 3.4.19.9), proteases or peptidases such as papain (E.C. 3.4.22.2), bromelain (E.C. 3.4.22.32), ficin (E.C. 3.4.22.3), trypsin (E.C. 3.4.21.4), chymotrypsin (E.C. 3.4.21.1), subtilisin (E.C. 3.4.21.62) and elastase (E.C. 3.4.21.37), and lipases (E.C. 3.1.1.3), such as lipase from porcine pancreas, *Candida rugosa*, *Thermomyces lanuginosa*, or *Rhizomucor miehei*. Increased specificity of the enzyme for the cysteine derivative will result in greater efficiency of reaction.

The enzymes may be isolated from natural sources, or may be recombinantly produced, including mutants of naturally occurring enzymes.

γ-Glutamyltranspeptidases (E.C. 2.3.2.2)

In nature γ-glutamyltranspeptidases (γ-GTs) catalyse the transfer of the γ-glutamyl moiety of glutathione to an acceptor which may be water, an amino acid, or di- or tri-peptide. These enzymes possess specific donor and acceptor sites, increasing the probability of aminolysis rather than hydrolysis, allowing the use of equimolar concentration of substrates in water with relatively high synthetic yields. Furthermore, protection strategies that are essential for the chemical synthesis of GGC, and which are also often required when using general proteases is unnecessary with the γ-GT catalysed reaction, due to its high specificity for the substrates.

Biological sources containing high levels of γ-GT have been identified in animals (*Ascaris suum*, fresh cow's milk, bovine kidney, human kidney, ovine kidney, porcine kidney, rat kidney, rat hepatoma, rat pancreas), bacteria (*Actinobacillus actinomycetemcomitans*, *Bacillus subtilis* Natto (Supernatant), *Escherichia coli*, *Fusobacterium nucleatum*, *Proteus mirabilis*), fungi (*Agaricus bisporus*, *Aspergillus oryzae*, *Morchella esculenta*, *Penicillium roqueforti*, *Saccharomyces*

*cerevisiae*) and plants (ackee seeds, kidney bean fruit). A convenient source of γ-GT is the whey fraction of cow's milk. However, investigation of alternative γ-GT sources may provide more readily available enzymes and/or enzymes with better parameters, such as cysteine specificity.

γ-Glutamyltranspeptidase may be most conveniently obtained from the whey fraction of bovine milk by using low-cost procedures known in the art such as, for example, concentration by ultrafiltration, salting-out, solvent precipitation, and proteolytic digestion (to remove contaminating proteins) techniques, or combinations thereof. The purified γ-GT may be immobilized onto a suitable resin bead substrate contained in a reaction column, thus allowing a continuous flow process, with the advantage of increased enzyme stability and the ability to re-use the immobilized γ-GT for multiple process batches.

γ-Glutamylhydrolases (E.C. 3.4.19.9)

γ-Glutamylhydrolases catalyse the removal of poly-γ-glutamate or γ-glutamate from pteroyl poly-γ-glutamate to yield pteroyl glutamate (Folic acid). As the enzyme has specificity towards γ-glutamyl bonds it may be used in reverse for transfer of γ-glutamyl groups to acceptor molecules.

Proteases and Peptidases

Many proteases and peptidases, although hydrolytic in nature, may be used to catalyse the reverse, synthetic reaction if appropriate conditions are provided, including reduction of water potential (so as to favour condensation over hydrolysis), and reduced temperature. Proteases and peptidases contemplated within the scope of the present invention may include proteases with esterase activity such as papain (E.C. 3.4.22.2), bromelain (E.C. 3.4.22.32), ficin (E.C. 3.4.22.3), trypsin (E.C. 3.4.21.4), chymotrypsin (E.C. 3.4.21.1), subtilisin (E.C. 3.4.21.62) and elastase (E.C. 3.4.21.37). The major advantage of using γ-glutamyltranspeptidase over these enzymes is that the reaction environment for these enzymes may require the addition of a high proportion of water miscible solvents (e.g. DMF) to favor the synthetic reaction, whereas, the reaction catalysed by γ-GT can be performed in 100% water.

Lipases (E.C. 3.1.1.3)

Similar to the proteases, although hydrolytic in nature, lipases may be used to catalyse the reverse, synthetic reaction if appropriate conditions are provided, including reduction of water concentration (so as to favour condensation over hydrolysis), and reduced temperature. The lipases have no restricted specificity for the α-carboxyl, unlike proteases, which may provide useful activity towards the γ-carboxyl of glutamic acid. Lipases contemplated within the scope of the present invention may include any suitable lipase, such as lipases from porcine pancreas, *Candida rugosa*, *Thermomyces lanuginosa*, or *Rhizomucor miehei*. The major advantage of using γ-glutamyltranspeptidase over these enzymes is that the reaction environment for these enzymes may require the addition of a high proportion of water miscible solvents (e.g. DMF) to favor the synthetic reaction, whereas, the reaction catalysed by γ-GT can be performed in 100% water.

Enzyme Immobilisation

The enzyme for use in the processes of the present invention may be immobilised to any appropriate support using methods and materials as are known in the art, and as described in, for example, Wiseman, A. (1995) *Handbook of Enzyme Biotechnology* (London, Ellis Horwood). The main criteria for an immobilisation matrix in relation to the proposed process are for it to:

1. Have a high enzyme binding capacity;
2. Maintain the stability of the enzyme under the reaction conditions and be able to be reused;
3. Be sufficiently robust to withstand a fluidised bed reaction; and
4. Be cost effective.

For example, the enzyme may be immobilised on commercially available activated supports such as Eupergit® activated resins (for example, Eupergit® C250L activated immobilising resin beads) using the instructions provided, optionally employing appropriate spacers. Alternatively, the enzyme may be immobilised to a desired surface, typically chromatographic support beads, using known diimide, epoxy or cyanogen bromide chemistries.

Transpeptidation Substrates

γ-Glutamyl Donors

Any suitable γ-glutamyl donor which meets the following criteria is contemplated by the present invention:
 adequate solubility in the solvent system (>0.1M);
 adequate activity of the enzyme with the γ-glutamyl donor; and
 any derivatizing groups must be easily removed to release the free γ-glutamylcysteine. For example, derivatizing groups such as benzyloxycarbonyl are unsuitable where the γ-glutamyl acceptor has one or more thiol groups, as removal of this group requires the use of a platinum catalyst which is poisoned by thiol groups.

Chemical derivatization of the donor substrates may affect the relative activity of the γ-glutamyl transferring enzyme. For example, with γ-GT, the derivatization of glutamic acid with γ-esters possessing a stronger electron withdrawing effect than the γ-ethyl ester may result in further increases in the aminolysis reaction. The γ-benzyl and γ-p-nitrobenzyl esters of glutamic acid (both having strong electron withdrawing groups) should therefore provide increased aminolysis, however solubility (<30 mM) in the solvent system has been found to be poor. Activated esters such as the p-chlorophenyl and cyanomethyl esters may be suitable derivatives for esterase enzymes with poor activity. The major limitation on the selection of ester is the cost of the derivative and its effect on solubility.

Although γ-GT has an absolute requirement for a free α-amino group on the γ-glutamyl donor, the α-carboxyl can be derivatized without loss of activity. Also, α-methyl esterification (as present in, for example, the glutamic acid α,γ-diethyl ester) may inhibit the autotranspeptidation reaction.

Examples of γ-glutamyl derivatives that are suitable donors for the transpeptidation include:
 a Glutamic acid-γ-ethyl, methyl, propyl or other water soluble ester
 Glutamic acid γ-ethylene glycol ester
 Glutamic acid methoxyethanol or ethoxyethanol esters
 Glutamic acid-γ-p-chlorophenyl ester
 Glutamic acid-γ-cyanomethyl ester
 Glutamic acid α,γ-diethyl ester (or dimethyl)
 γ-Glutamyl ethyl, methyl, propyl or other water soluble amide Synthesis of γ-Glutamyl Donors a. γ-Glutamyl Esters γ-Alkyl esters of glutamic acid may be readily prepared by standard esterification reaction of glutamic acid with the appropriate alkyl alcohol, under acidic conditions. For example, glutamic acid esters may be synthesised according to a conventional method such as a Fischer esterification where an amino acid is dissolved in the pertinent alcohol (e.g. ethanol for the ethyl ester) in the presence of a mineral acid (e.g. hydrogen chloride or sulphuric acid) as the catalyst. The γ-carboxyl group of glutamic acid is preferentially esterified as it is more basic than the α-carboxyl group. Only after extended reaction time and heating is the α,γ-diester formed.

For the synthesis of glutamic acid γ-ethyl ester, the following procedure may be used, optionally scaled up. A suspension of glutamic acid (35 g; 24 mmol) in anhydrous ethanol (350 mL) containing dissolved dry hydrogen chloride gas (23 g; 63 mmol) is prepared with stirring at room temperature until all of the solids have dissolved (approximately 20 minutes). The solution is diluted to 1 L with anhydrous ethanol, and triethylamine added drop-wise until the solution is alkaline. The mixture is allowed to stand overnight at 4° C. resulting in a crystalline suspension which can be collected by filtration in a buchner funnel, followed by washing successively with cold anhydrous ethanol and then ether. The filter cake is then dried under reduced pressure over silica in a desiccator.

Synthesis of the α,γ-diethyl ester may be done by a similar route by saturating the glutamic acid/anhydrous ethanol solution with hydrogen chloride gas and heating to a gentle reflux for 3 hours and then cooling to room temperature for approximately 1 hour prior to the dilution to 1 L with anhydrous ethanol.

Alternatively, glutamic acid γ-ethyl ester may be prepared by a slightly modified procedure in which, instead of dry hydrogen chloride gas, sulphuric acid (98%) is added drop-wise to a stirred suspension of glutamic acid in anhydrous ethanol and the mixture reacted for about two hours at room temperature. The mixture is then carefully neutralised with sodium hydroxide below 10° C. while keeping the ethanol concentration at about 60% v/v or higher (sodium sulphate is insoluble in this solution, but the glutamic acid γ-ethyl ester is soluble), and the filtrate concentrated and crystallised by the addition of ethanol to about 80% v/v. Instead of crystallisation, the ethanol may be distilled off, and the glutamic acid γ-ethyl ester solution, optionally diluted, may be used directly in a process of the invention.

b. γ-Glutamyl Amides

Several γ-amides of glutamic acid may be suitable donors for the transpeptidation reaction. For example the amide L-γ-glutamyl-p-nitroanilide used in Example 2 was demonstrated to be an effective γ-glutamyl donor. However, the need for complex protection and de-protection chemistry used to synthesize L-γ-glutamyl-p-nitroanilide and many other similar γ-glutamyl amides preclude their usefulness on economical grounds. Several simple γ-glutamyl amides can be synthesized without the need of protective groups, these are the strongly basic amines such as methylamine and ethylamine which can form γ-glutamyl amides spontaneously when reacted with pyrrolidinecarboxylic acid (a cyclic derivative formed by the loss of water when glutamic acid is heated to 180° C.). For example Lichtenstein (Lichtenstein, N. Preparation of γ-alkylamides of glutamic acid. *Journal of the American Chemical Society,* 1942. 64 p. 1021-1022) described the synthesis of several γ-glutamyl alkylamides (methyl and ethyl) by treating an aqueous solution of pyrrolidinecarboxylic acid with the pertinent amine at 37° C. for 10 days. Glutamine was not obtained by the treatment of pyrrolidinecarboxylic acid with aqueous ammonia. The simplest γ-glutamyl amide, glutamine, used in Example 3 was demonstrated to be an ineffective γ-glutamyl donor.

Cysteine Derivatives

Cysteine is a poor γ-glutamyl acceptor for the reaction catalysed by γ-glutamyltranspeptidase, this enzyme being approximately 100-fold more specific for cystine as the acceptor. However, cystine is poorly water soluble (approximately 5 g/L at 37° C. and pH 9.1, the solubility being lower at lower temperatures and pH values) and, as a result, cystine is not suitable for use as a γ-glutamyl acceptor for an industrial scale process.

Chemical derivatization of the acceptor substrate (cysteine derivative) may also affect yields of γ-glutamylated derivatives. For best efficiency of the reaction, the cysteine derivative should ideally meet the following criteria:

adequate solubility in the solvent system (>0.1M);
adequate activity of the enzyme with the γ-glutamyl acceptor; and
any protecting and/or solubilising groups on the acceptor must be easily removed to release free the γ-glutamylated derivative (e.g. derivatives such as S-benzyl cysteine are unsuitable because they require harsh chemical conditions for removal).

In the course of these investigations, several cyst(e)ine derivatives have been identified as potential acceptors. These include: the mixed disulphide of cysteine and mercaptoethanol (Cys-Merc), the mixed disulphide of cysteine and thioglycolic acid, the salt of S-sulpho-cysteine, and the monomethylester (half ester) of cystine which can possibly be synthesized by partial esterification of cystine. All three derivatives should have good aqueous solubility and are easily deprotected by either reduction with excess thiol or electrochemically. The derivative S-acetamidomethylcysteine has been demonstrated to have high aqueous solubility (2 M possible), and is one of the most commonly used protected forms of cysteine in industrial synthesis of pharmaceutical peptides. Removal of the S-acetamidomethyl group is effected by treatment with iodine and results in the formation of the corresponding disulphide.

Cysteine derivatives which result in a reduction of the $pK_a$ of the α-amino may significantly increase the aminolysis reaction. Due to its closer proximity to the α-amino group, derivatization of the α-carboxyl group of cyst(e)ine is likely to have a greater effect on its $pK_a$ than S-derivatization. Ideally, the α-carboxyl group of cyst(e)ine would be derivatized by a strong electron-withdrawing group such as an amine. However, its is suitability would strongly depend on how easily the group is removed, with protease-catalysed deprotection being a possible option.

Examples of suitable cysteine derivatives for the transpeptidation reaction include
Mixed disulphides of cysteine and low molecular weight water-soluble thiols;
S-Acetylcysteine;
S-Acetamidomethylcysteine;
S-Methoxycarbonylsulphenylcysteine;
S-Sulphocysteine;
Cystine dimethyl ester
Cystine monomethyl ester Water-soluble thiols for preparation of mixed disulphides may include any appropriate low molecular weight water-soluble thiol, such as thioglycolic acid, cystamine, thioacetic acid, methanethiol or ethanethiol. An example of a suitable mixed disulphide of cysteine for use in the processes of the present invention is cysteine-mercaptoethanol mixed disulphide.

Synthesis of Cyst(e)ine Derivatives

The effective protection of the thiol group of cysteine is an ongoing problem in peptide chemistry and a thorough review of the derivatizing/protecting groups has been performed by Kudryavtseva (Kudryavtseva, E. V., et al. Peculiarities of synthesis of the cysteine-containing peptides. *Uspekhi Khimii,* 1998. 67(7): p. 611-630). However, the major disadvantage with nearly all of the cysteine derivatives described in the literature is that they are designed to be soluble in non-polar organic solvents, thus rendering them unsuitable for the presently described invention in which water is the solvent of choice. Several water-soluble derivatives of cysteine have been identified and are listed below.

a. Mixed Disulphides

Numerous options exist for the formation of mixed disulphides including; reduction of the S-sulpho-cysteine intermediate with 2-mercaptoethanol (Stapleton, I. W., et al. Amino acids and peptides 0.9. Some unsymmetrical disulphides derived from cysteine. *Australian Journal of Chemistry*, 1962. 15(3): p. 570), reduction of the S-(2-hydroxyethyl)-methanethiolsulphonate intermediate with cysteine (Nagasawa, H. T., J. F. Cohen, and W. B. Rathbun, Mixed disulfides of L-cysteine and its derivatives with 2-mercaptoethanol. *Organic Preparations and Procedures International* (Briefs). 1996. 28(2): p. 237-241), and diaquacobinamide catalysed mixed disulphide formation (Budy, B., et al., A facile synthesis of homocysteine-cysteine mixed disulfide. *Analytical Biochemistry*, 2001. 291(2): p. 303-305). The mixed disulphide of cysteine and thioglycolic acid can be prepared as described in, for example, Greenstein, J. P. and M. Winitz, *Chemistry of the amino acids*. Vol. 3. 1961, New York: John Wiley & Sons. p. 1879-1928. Other methods for the formation of mixed disulphides include: Reaction of cysteine with excess mercaptoethanol and cyanogen bromide (Abe, O., et al. Synthesis of mixed disulfides with cyanogen-bromide and its consequences for elucidation of protein structure. *Journal of Organic Chemistry* 1974. 39(2): p. 253-255). Reaction of either cysteine or mercaptoethanol with an alkoxycarbonylsulfenyl chloride to form a S-alkyloxycarbonylsulphenyl derivative, which reacts easily with thiols to form mixed disulphides (Rietman, B. H., et al. A facile method for the preparation of S-(alkylsulfanyl)cysteines. *Synthetic Communications*. 1994. 24(9): p. 1323-1332).

One method for the synthesis of a mixed disulphide of cysteine is the use of a thiolsulphinate (mono disulphide oxide) intermediate as first described by Schoberl (Schoberl, A., et al. Synthese und reaktions weise von unsymmetrischen disulfiden 0.6. Aminocarbonsauren und haarkeration mit unsymmetrisch eingebauten disulfidaustausches. *Annalen Der Chemie-Justus Liebig*. 1958. 617(1-3): p. 71-88).

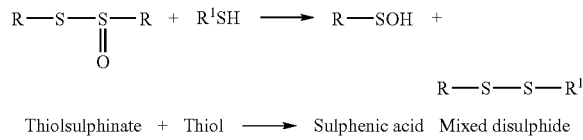

Thiolsulphinate + Thiol ⟶ Sulphenic acid  Mixed disulphide

The resulting sulphenic acid can be further reduced by a thiol to form a mixed disulphide as follows:

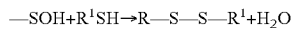

In the above reaction scheme cysteine or the desired derivatizing group (e.g. mercaptoethanol) may be either R or $R^1$. Cystine thiolsulphinate and most other thiolsulphinates can be synthesised by oxidation with an organic peracid (e.g. peracetic acid, performic acid, and monoperoxyphthalate) as demonstrated by: (Savige, W. E., et al. The S-monoxides of cystine, cystamine and homocysteine. *Tetrahedron Letters*. 1964. (43-4): p. 3289-3293), (Walti, M., et al. Synthesis of isomers of mono- and di-hydroxy-analogues of cystine and comparison with metabolites excreted in urine. *Journal of the Chemical Society C-Organic*, 1971. 12: p. 2326) and (Batistaviera, F., et al. Solid-phase thiolsulfinates for the reversible immobilization of thiols. *Applied Biochemistry and Biotechnology*. 1994. 44(1): p. 1-14).

Another method for the synthesis of a mixed disulphide of cysteine is copper ion catalysed air/$O_2$ oxidation as follows:

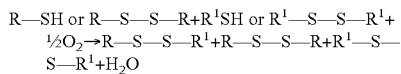

R—SH may be mercaptoethanol, or R—S—S—H may be 2,2'-dithiodiethanol (DTDE), and $R^1$SH may be cysteine or $R^1$—S—S—$R^1$ may be cystine. A 3-4 molar excess of R—SH or R—S—S—H (based on R—SH) is required for mixed disulphide (R—S—S—$R^1$, Cys-Merc) to be the predominant reaction product. As lower starting thiol concentrations are preferred for quicker reaction completion, and a 3-4 molar excess of R—SH or R—S—S—H (based on R—SH) is required to avoid cystine precipitation an oxidation involving R—S—S—R (such as DTDE) and $R^1$SH (cysteine) will be quicker than a reaction between R—SH and $R^1$—S—S—$R^1$, which will in turn be quicker than a reaction between R—SH and $R^1$—SH. Cystine contamination of the resulting mixed disulphide is also undesirable as it may result in undesired production of GGC-cystine in a process of the invention. Using 3-4 molar excesses of R—SH or R—S—S—H (based on R—SH) will reduce the risk of cystine contamination.

The reaction occurs in the presence of copper II ($Cu^{2+}$) ions at pH 8.5 up to pH 9.0 with vigorous aeration, for example by bubbling air into the reaction mixture through a frit. If electrochemical reduction is to be employed for later reduction of the GGC derivative to the thiol form, copper(II) ion removal is necessary at the completion of the synthesis of Cys-Merc. This may be effected by, for example, passage through a column of chelating resin with a high selectivity for copper (II) ions such as Sepharose with immobilized iminodiacetic groups. Effective removal is observed visually in the column by the strong blue coloration of the resin imparted by the chelation of copper ions which is not allowed to reach the end of the resin bed before the complete elution of the reaction mixture.

Mixed disulphide of cysteine produced by the above method may be purified and crystallised or the reaction mixture may be used directly in a process of the invention. For example, Cys-Merc mixed disulphide may be crystallized by adjustment to pH 5.2 (isoelectric point of Cys-Merc) with acetic acid followed by the addition of 3 volumes of acetone at −20° C. which results in a rapid deposition of Cys-Merc crystals.

The synthesis of a mixed disulphide of cysteine may also be achieved by the use of electrochemical oxidation. This is essentially a reverse of electrochemical reduction reaction as discussed further below and Example 12, but replacing GGC with cysteine. The oxidation reaction which is conducted at the anode for the synthesis of disulphides from thiols has been reported for the synthesis of mixed disulphide (Do, Q. A new electrochemical method of preparation of unsymmetrical disulfides *Tetrahedron Letters*, 1997, 38, 3383-3384).

b. S-Acetamidoalkyl Derivatives

The S-acetamidoalkyl derivatives of cysteine are most conveniently prepared by reaction of the pertinent N-hydroxyalkyl)acetamide with cysteine hydrochloride in dilute hydrochloric acid. For example Milkowski (Milkowski, J. D., et al. Thiol protection with the acetamidomethyl group —S-acetamidomethyl-1-cysteine hydrochloride. *Organic Syntheses*, 1988. 6: p. 5-8) described the synthesis of S-acetamidomethylcysteine using N-(hydroxymethyl)acetamide and is depicted in the reaction scheme below.

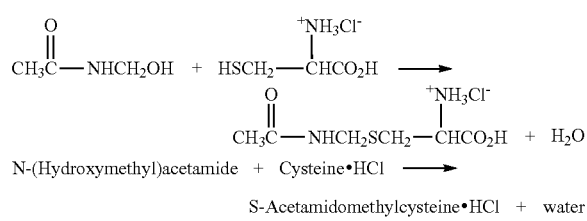

N-(Hydroxymethyl)acetamide + Cysteine•HCl ⟶ S-Acetamidomethylcysteine•HCl + water The zwitterionic form S-acetamidomethylcysteine may be obtained readily from the hydrochloride by neutralization with sodium hydroxide, by ion-exchange chromatography, or by precipitation from isopropanol with pyridine. S-acetamidomethylcysteine can also be prepared from N-(hydroxymethyl)acetamide under anhydrous conditions in liquid hydrogen fluoride and in trifluoroacetic acid. Removal of the S-acetamidomethyl group is effected by treatment with iodine and results in the formation of the corresponding disulphide.

c. S-Sulphocysteine

Several options exist for the formation of S-sulphocysteine including; treatment of an ammonia solution of cystine with a large excess of ammonium sulphite (Clarke, H. T. *Journal of Biological Chemistry*, 1932. 97: p. 235), conversion of cystine or cysteine by sodium sulphite in the presence of cupric ions (Moore, W., et al. Inactivation of γ-glutamylcystine synthetase, but not glutamine synthetase, by S-sulphocystine and S-sulphohomocystine. *The Journal of Biological Chemistry*, 1987.262: p. 16771-16777) or by the action of sodium tetrathionate on cysteine (Maugras, I., et al. Peptide-synthesis using novel S-sulphocysteine derivatives. *International Journal of Peptide and Protein Research*, 1995. 45(2): p. 152-156). Following the latter option, depicted in the reaction scheme below, the monosodium salt of S-sulphocysteine can be prepared at large scale and in good yield.

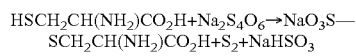

Cysteine+Sodium Tetrathionate→Sodium S-Sulphocysteine+Sulphur+Na Sulphite

The S-sulpho group is easily removed as sulphur dioxide gas under standard reducing conditions as described by Jocelyn, P. C. (Jocelyn, P. C., Chemical reduction of disulfides. *Methods in Enzymology*, 1987.143: p. 246-56).

d. Alkyl Esters of Cystine

Cystine esters may be synthesised according to a conventional method such as a Fischer esterification where cystine is dissolved in the pertinent alcohol (e.g. methanol for the methyl ester) in the presence of a mineral acid (e.g. hydrogen chloride or sulphuric acid) as catalyst. The use of a large excess of alcohol and a long reaction time under reflux results in the formation of cystine dialkyl ester. For example the synthesis of cysteine dimethyl ester dihydrochloride using methanol is depicted in the reaction scheme below.

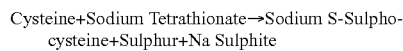

Cystine+HCl+Methanol→Cystine dimethyl ester dihydrochloride+Water

Under similar reaction conditions the use of half the stoichiometric amount of alcohol in a chloroform solution of cystine results in formation of cystine monoalkyl ester. The free base form of the ester may be obtained readily from the hydrochloride by neutralization with sodium hydroxide, by ion-exchange chromatography, or by precipitation from isopropanol with pyridine. Removal of the ester is effected by saponification with an excess of sodium hydroxide.

e. S-Alkoxycarbonylsulphenyl Derivative

The S-alkoxycarbonylsulphenyl derivatives of cysteine are most conveniently prepared by reaction of the pertinent alkoxycarbonylsulphenyl chloride with cysteine hydrochloride in a methanol solution. For example Rietman (Rietman, B. H. A facile method for the preparation of S-(alkylsulfanyl)cysteines. *Synthetic Communications*, 1994. 24(9): p. 1323-1332) described the synthesis of S-(methoxycarbonylsulphenyl)cysteine.HCl using methoxycarbonylsulphenyl chloride and is depicted in the reaction scheme below.

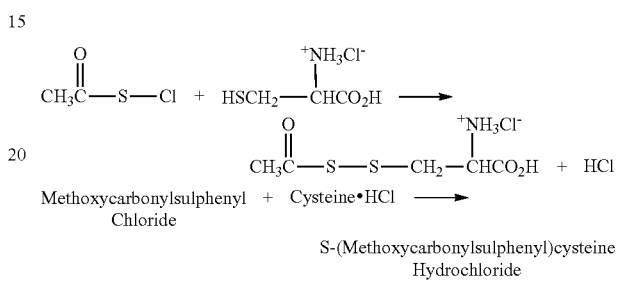

Methoxycarbonylsulphenyl Chloride + Cysteine•HCl ⟶ S-(Methoxycarbonylsulphenyl)cysteine Hydrochloride The zwitterionic form may be obtained readily from the hydrochloride by neutralization with sodium hydroxide, by ion-exchange chromatography, or by precipitation from to isopropanol with pyridine. The S-Methoxycarbonylsulphenyl group is easily removed under standard reducing conditions as described by Jocelyn, P. C. (Jocelyn, P. C., Chemical reduction of disulfides. *Methods in Enzymology.*, 1987. 143: p. 246-56).

f. S-Acetylcysteine

The preparation of S-acetylcysteine can be performed according to two procedures: either by acid catalysed S-esterification of cysteine with thioacetic acid (Uotila, L. Preparation and assay of glutathione esters. *Biochemistry* 1973. 12 p. 3938-3943), or by the action of acetyl chloride on cysteine with trifluoroacetic acid as solvent to protect the amino group of cysteine. The latter option, depicted in the reaction scheme below, was first demonstrated in a patent by Galzigna (Galzigna, L. A process for the preparation of glutathione S-acyl derivatives. 1990. PCT/EP91/01154), which describes a method for S-acylating glutathione with high yield and selectivity.

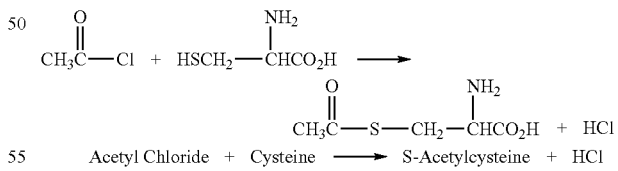

Acetyl Chloride + Cysteine ⟶ S-Acetylcysteine + HCl

The S-acetyl group can be removed by either acidic or alkaline hydrolysis.

Reaction Conditions

The γ-glutamyl donor (such as glutamic acid γ-ester) and the γ-glutamyl acceptor/cyst(e)ine derivative (such as cysteine-mercaptoethanol mixed disulphide) can be mixed (for example, in an equimolar concentration) in the presence of the selected enzyme under conditions which favour the enzyme catalyzed formation of an α,γ-amide linkage (peptide bond) between the cyst(e)ine derivative and the γ-glutamyl donor. Where the γ-glutamyl donor is a glutamic acid γ-ester, an appropriate enzyme would exhibit esterase activity, such as γ-glutamyltranspeptidase.

a. pH

The reaction environment should have a pH which is within about 1 to 2 pH units of the pH optimum for transfer of the γ-glutamyl group to the cysteine derivative by the subject enzyme. However where the enzyme has a relatively flat pH activity profile, broader pH ranges may be applicable. Reaction pH may also affect the reactant concentrations, and this may be a determining factor, and the enzyme's pH optimum may not necessarily provide the optimum reaction conditions. Once the basic enzyme and reactant parameters are known, pH optimisation may be readily performed by those of skill in the art by straight forward procedures and modeling.

The pH optimum for this reaction will not necessarily be the same as the pH optimum for the reverse reaction.

Bovine γ-GT has a pH optimum of approximately pH 8.8-pH 9.0, but may be denatured at pH values above about pH 9.5. Accordingly, the reaction environment pH where bovine γ-GT is used may be from about pH 7 to about pH 9.5, such as from about pH 7.5 is to about pH 9.4, from about pH 7.9 to about pH 9.3, from about pH 8.0 to about pH 9.0, from about pH 8.1 to about pH 9.2, from about pH 8.3 to about pH 9.1, from about pH 8.5 to about pH 9.0, about pH 8.0, about pH 8.1, about pH 8.2, about pH 8.3, about pH 8.4, about pH 8.5, about pH 8.6, about pH 8.7, about pH 8.8, about pH 8.9 or about pH 9.0.

Many hydrolases, such as γ-glutamyl hydrolase, carboxypeptidases, and aminopeptidases typically have pH optima below neutral, and therefore the optimum pH may be between about pH 2.5 and about pH 7, depending on the enzyme.

In the present studies, using bovine γ-glutamyltranspeptidase, relatively high concentrations of buffering agent (DEA, 0.2M) were found to be required to maintain the reaction pH at around 8.5-9, which significantly increased the ionic strength of the reaction mixture, and this significantly affects the apparent activity of γ-GT, and may affect the activity of other enzymes which may be used in the processes of the present invention. The use of a pH-stat, a reaction vessel equipped with a pH probe and pumps for the addition of acid or base to maintain the pH to a certain set point, should eliminate the need for buffering and decrease the ionic strength of the reaction mixture.

At a pH of 8.5 or greater, the amidase activity of bovine γ-glutamyltranspeptidase has been found to result in hydrolysis of the γ-glutamyl derivative product (see item (d) below), which can be reduced or avoided by use of a water-miscible solvent, such as dimethylformamide. However, with better control over reaction pH, such as attainable with a pH-Stat, a lower pH can be selected—using a pH-Stat and a pH of 8.0 the secondary hydrolysis of the γ-glutamyl derivative product was not found to occur to the same degree.

b. Temperature

Generally speaking, the temperature to be employed will be that which provides the greatest rate of reaction, although this may be affected by the improvement to be gained by increased temperature relative to heating costs, stability of the enzyme, reactants and/or product. Reaction temperature may be readily optimised by those skilled in the art by straight forward procedures and modeling once the basic enzyme and reactant parameters are known.

For the reaction catalysed by γ-GT, the optimum temperature was found to be about 37° C., however, temperatures from about 20° C. to about 50° C., such as about 20° C., 22° C., 24° C., 26° C., 28° C., 30° C., 32° C., 34° C., 36° C., 38° C., 40° C., 42° C., 44° C., 46° C., 48° C., or 50° C. may be employed.

Kinetically controlled reactions using proteases at lower reaction temperatures (−15 to is 20° C.) both with immobilized and soluble enzyme may also increase yields, possibly due to tighter binding of the acceptor to the enzyme at lower temperatures. Lower temperatures may also offset the deleterious effect organic co-solvents have on enzymes by increasing the dielectric constant of the medium. Lowering the reaction temperature may however reduce the solubility of the substrates.

c. Reactant Concentration

Generally speaking, the reactants should be provided in the reaction environment at a concentration which provides the maximum rate of reaction. However, the concentration will also be dictated by the reaction time, which in batch-wise processes will be determined by the final product concentration achievable or desired, and which in continuous processes will also be subject to limitations of residence time in the reactor. Particularly for continuous reactions optimisation will be necessary so as to minimise concentration of unreacted components in the eluate stream, but this can be achieved by straight forward procedures and modelling once the basic enzyme parameters are known and/or can be readily determined by those skilled in the art.

Reactant concentration will also depend on cost of each reactant and optimisation of yield of the reaction on the basis of the most expensive reactant. Again, once the basic enzyme parameters are known, models and procedures for optimising such reactions are available and/or can be readily determined by those skilled in the art.

Typically, where the reaction is catalysed by γ-glutamyltranspeptidase, a γ-glutamyl methyl or ethyl ester is used as γ-glutamyl donor, and cysteine-mercaptoethanol mixed disulphide is used as cysteine derivative, the concentration of the γ-glutamyl donor and of the cysteine derivative may be, independently, up to about 4M, such as about 2M, about 1.75M, about 1.5M, about 1.25M, about 1M, about 900 mM, about 800 mM, about 700 mM, about 600 mM, about 500 mM, about 400 mM, about 300 mM, about 200 mM, or about 100 mM.

Maximum reactant concentration may also be affected by the presence of water-miscible solvent, or other components or parameters (such as temperature) of the reaction environment. For example, cysteine-mercaptoethanol mixed disulphide is less soluble in a reaction environment comprising DMF as a water-miscible solvent than in water alone, whereas less water-soluble reactants may be more soluble in such environments than in water.

d. Solvent

With a number of enzymes, the presence of water may promote hydrolytic reactions. This is the case with proteases, peptidases, γ-glutamylhydrolase, and γ-glutamyltranspeptidase. In such situations the reaction (transfer of the γ-glutamyl group to the cysteine derivative) efficiency may be improved by including a water-miscible solvent to lower the water concentration. Also, inclusion of water-miscible solvents in reaction mixtures comprising γ-glutamyltranspeptidase has been found to inhibit the amidase reaction (removal of the γ-glutamyl moiety from GGC) while leaving significant esterase activity.

Suitable water-miscible solvents may include, for example, 1,3-butanediol, 1,4-butanediol, acetone, acetonitrile, dimethylsulphoxide, dioxan, dimethylformamide (DMF), ethanol, ethoxyethanol, ethyleneglycol, glycerol, isopropanol, methanol, and methoxyethanol.

As mentioned in item (a) above, if appropriate pH control can be provided, a lower reaction pH can be used, such as a pH of about 8.0, at which the amidase reaction has been found to occur to a lesser degree, without the need for addition of a water-miscible solvent.

e. Reaction Time

Reaction time will be dependent on whether a batch-wise or continuous process is utilized, with the enzyme concentration in a batch process, and the column residence time in a continuous process being the determining factors. Optimization of reaction time will be necessary in both cases, and will be readily determined by those skilled in the art by standard trial and experimentation.

Antimicrobials may be included in the reaction solution(s) in order to reduce or avoid microbial contamination of the reaction which may result in degradation of the enzyme, reactants or products.

f. Process

The process may be performed in either a fed-batch or batch-wise process or in a continuous flow process utilizing a γ-GT immobilized reaction column.

i) Batch-Wise Process

Figure 4:
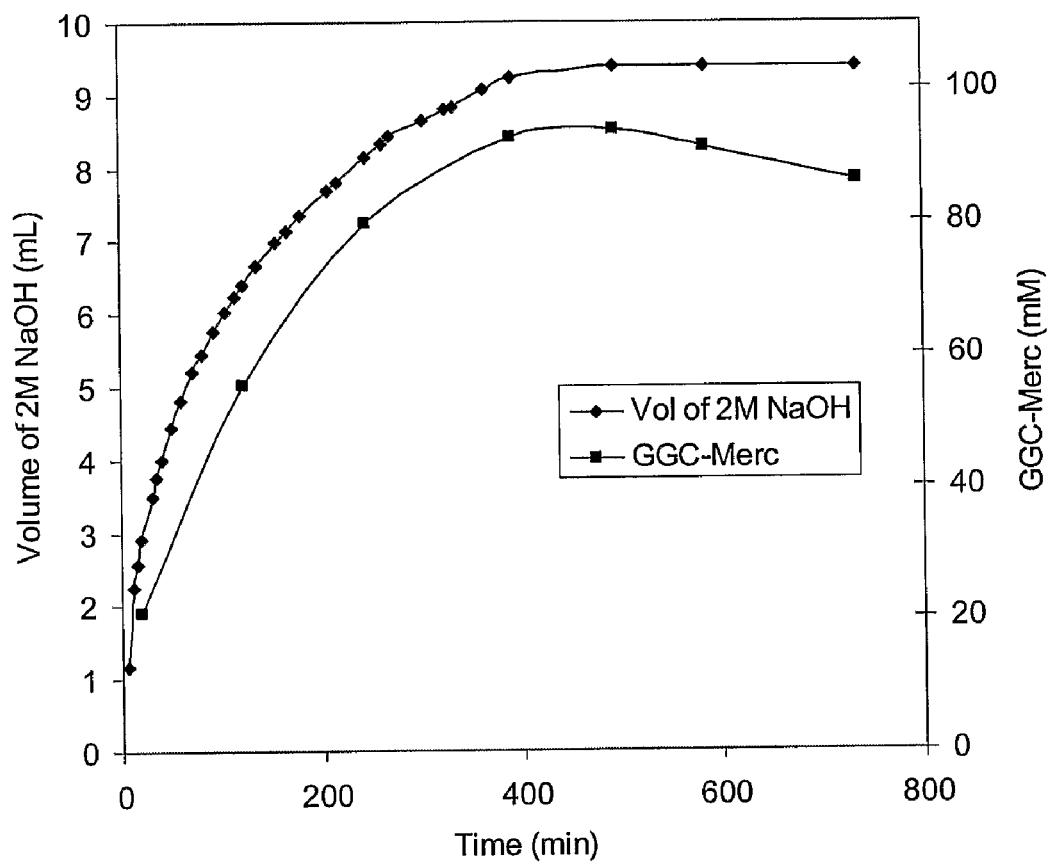
FIG. 4 is a graph of γ-GGC-mercaptoethanol disulphide production and sodium hydroxide addition to maintain pH8.0 in a process of the invention as described in Example 10.
Figure 5:
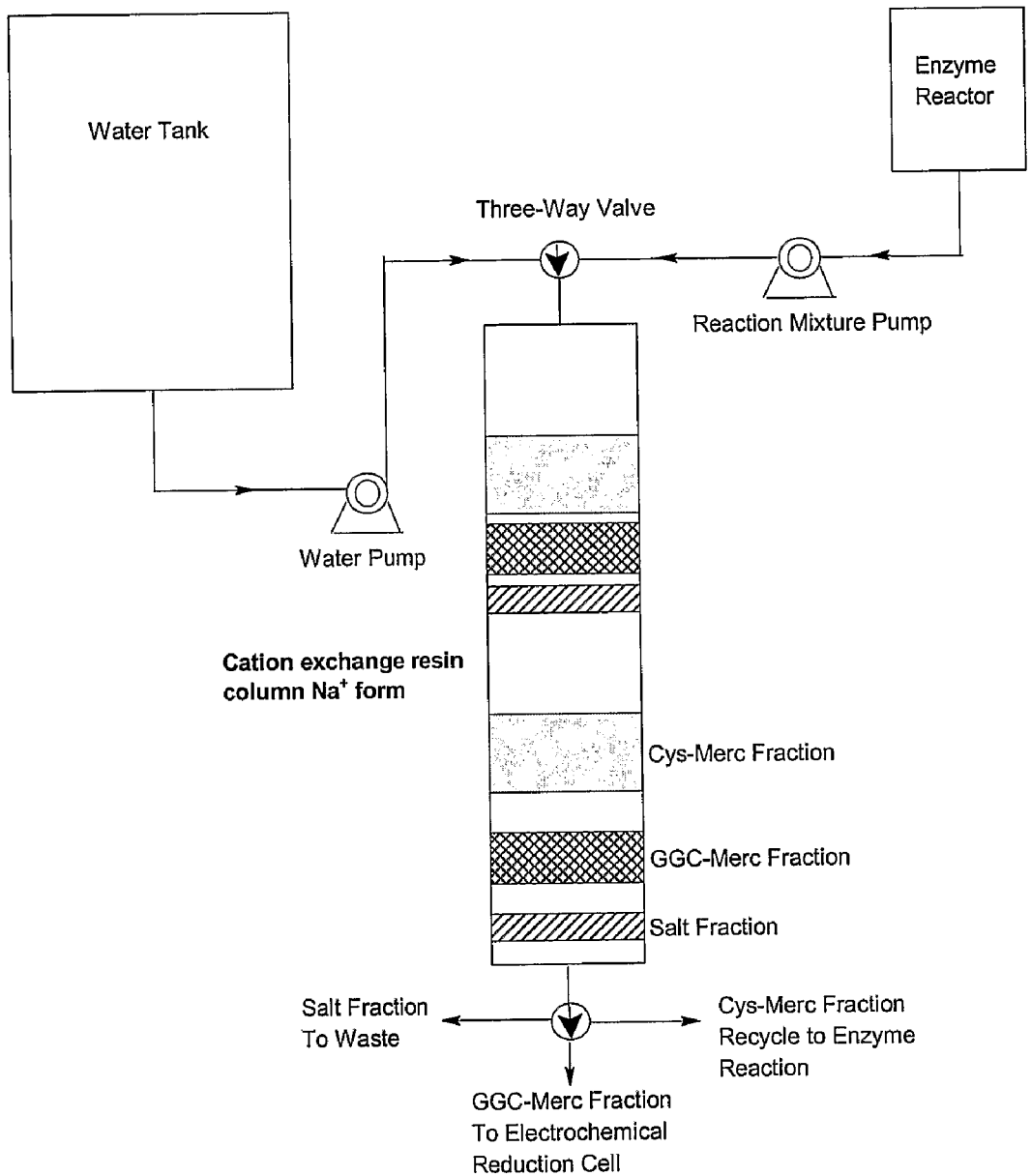
FIG. 5 is a schematic for continuous ion exclusion chromatography of reaction mixture prepared by a process according to the invention comprising γ-GGC-mercaptoethanol disulphide and reactants and by-products.

A batch-wise process for the industrial production of GGC using γ-GT, as shown in FIGS. 4 and 5, may consist of three major steps, although clearly a wide range of alterations or adaptations will be possible without affecting the nature of processes of the invention.

The preparation of a suitable γ-glutamyl derivative, such as described above would be one of the first steps. For example, glutamic acid and an alcohol, preferably ethanol, as starting materials are reacted in an alcoholic solution at 25° C. in the presence of a mineral acid to prepare a solution containing glutamic acid γ-ester. The excess acid is neutralized by the addition of a base. Excess alcohol is removed by evaporation and substituted with water to convert it to an aqueous solution of the glutamic acid γ-ester, preferably having a concentration of at least 0.2M.

The preparation of a suitable cysteine derivative, such as described above would be another of the first steps of the industrial production of GGC. For example, the starting material cysteine can be reacted with numerous derivatizing agents, some of which protect the thiol group (—SH) from oxidation to cystine, which is poorly soluble. Accordingly, it is preferable that the derivatizing group improves the aqueous solubility of cystine. One effective derivatizing group of cysteine identified here is the mixed disulphide of cysteine-mercaptoethanol (Cys-Merc). The derivative cysteine-mercaptoethanol may be synthesised by, for example, using a thiolsulphinate intermediate, or by copper ion catalysed air/$O_2$ oxidation of mercaptoethanol or DTDE and cysteine or cystine, as described above.

The preparation of the enzyme, ideally γ-glutamyltranspeptidase, would be another first step in the industrial production of GGC. γ-GT is most conveniently obtained from the whey fraction of bovine milk by using low-cost procedures known in the art such as, for example, concentration by ultrafiltration, salting-out, solvent precipitation, and proteolytic digestion (to remove contaminating proteins) techniques, or combinations thereof.

The second stage in the batch-wise process for the industrial production of GGC would involve the formation of the γ-glutamyl bond. The prepared aqueous solutions of the two derivatives of the amino acids are mixed together in approximately equimolar proportions in a suitable pH and temperature controlled vessel, and, where the reaction is catalysed by γ-glutamyltranspeptidase, the pH of the mixture is ideally adjusted to about pH 8.0 to about 9.0. Where the reaction pH is about 8.5 or higher, a water miscible organic solvent such as dimethylformamide may be added optionally to the reaction mixture up to a concentration of about 50% (v/v) prior to the addition of enzyme to improve product formation and prevent hydrolysis of the peptide product. Where the reaction pH is less than about 8.5, such as about 8.0, it has been found that it is not necessary to add a water-miscible solvent as the undesirable amidase hydrolysis of the γ-glutamylcysteine product occurs to a less significant degree. Prepared γ-GT, which may be lyophilized, is added to the reaction mixture to yield a final concentration of the order of 1-5 U/mL and progress of the reaction is monitored by sampling on an hourly basis. When the yield of γ-glutamylcysteine-mercaptoethanol disulphide has reached a maximum (about 30%), the reaction is stopped by adjusting the pH of the mixture to about pH 12 with concentrated sodium hydroxide.

The third stage of the industrial production of GGC would involve the removal of the mercaptoethanol group and purification of the final product or purification of the GGC-mercaptoethanol disulphide and removal of the mercaptoethanol group, followed by further purification. Several options for the purification of GGC or GGC-mercaptoethanol mixed disulphide from the reaction mixture are possible, including ion exchange or ion exclusion chromatography, electrodialysis, differential crystallisation, or combinations thereof, with removal of the mercaptoethanol group before or after such purification. Some appropriate lab-scale methods which may be scaled up for industrial use are detailed in Examples 12 to 14.

One sequence of steps from formation of GGC-mercaptoethanol disulphide to substantially pure GGC comprises electrochemical reduction of GGC-mercaptoethanol disulphide to cleave the mercaptoethanol group, followed by removal of mercaptoethanol from the reaction mixture. Mercaptoethanol removal may be achieved by partitioning with a non-polar solvent and the purified GGC precipitated by ethanol addition (to greater than 80% v/v).

Alternatively, cleavage of the mercaptoethanol group from GGC-mercaptoethanol disulphide may be performed by the induction of a disulphide interchange reaction. This is initiated by adjusting the pH of the reaction mixture to pH 12 and the reaction is monitored by HPLC analysis until no mixed disulphide is present (several hours). At the same time, water can be removed from the reaction mixture by evaporation under reduced pressure. The pH of the reaction mixture is then adjusted to pH 3 with acetic acid, which should be accompanied by the precipitation of unreacted cystine, which can be removed by filtration. The by-product 2-hydroxyethyl disulphide is partitioned into ethyl acetate by continuous counter current extraction of the filtrate and the volume of the resulting aqueous phase can be further reduced by evaporation under reduced pressure. The reaction by-products cystine and 2-hydroxyethyl disulphide may be optionally recycled for use in the next production batch. The purification of bis-γ-glutamylcystine can be effected by fractional crystallization, followed by an optional final polishing step of ion exchange chromatography.

ii) Continuous Process

A continuous process for the industrial production of GGC using γ-GT, as shown in FIGS. 4 and 5, may consist of three major steps, although clearly a wide range of alterations or adaptations will be possible without affecting the nature of processes of the invention.

The chemical derivatisation of glutamic acid and cysteine to form suitable substrates for the enzyme reaction are the same part of the first step described for the batch-wise process above. The preparation of the enzyme, ideally γ-GT, differs from the batch-wise process in that the enzyme is preferably immobilized on a solid substrate suitable for packaging in a continuous flow column. The second stage in the continuous process also differs from the batch-wise process in that reaction mixture is pumped through the immobilized enzyme column at a rate optimized for maximal yield of product. This processing option has several advantages over the batch-wise process including the ability to effectively reuse the column of immobilized enzyme without appreciable loss in enzyme activity and increased productivity per unit volume.

The preparation of immobilized enzyme would be a first step in the continuous process for the industrial production of GGC. γ-GT is most conveniently obtained from the whey fraction of bovine milk, as described above for the batch-wise process, but the soluble enzyme in the supernatant is immobilized by reacting with suitably activated resin beads. The resulting resin may contain approximately 350 U/g of γ-GT.

The next stage in a continuous process for the industrial production of GGC would involve the formation of the γ-glutamyl bond. The prepared aqueous solutions of the two derivatives of the amino acids (as described in the batch-wise process above) are mixed together in approximately equimolar proportions by pumping them through a suitable pH controlled continuous flow mixing device, and, where the reaction is catalysed by γ-glutamyltranspeptidase, the pH of the mixture is ideally adjusted to about pH 8.0 to about pH 9.0. Appropriate buffering may be required, as pH control in a column is difficult to achieve, and may be particularly important if a pH closer to 8.0 is used. A water miscible organic solvent such as dimethylformamide may be added optionally to the reaction mixture up to a concentration of about 50% (v/v), if a pH of about 8.5 or higher is employed, prior to the enzyme reaction to improve product formation and prevent hydrolysis of the peptide product. The prepared immobilized γ-GT enzyme resin beads are packed into a column equipped with a jacket thermostatted to about 37° C. and the above mixture pumped through the column at a rate in which the yield of γ-glutamylcysteine-mercaptoethanol on either substrates does not drop below a predefined set point (around 30%). If 50% DMF is not used as a co-solvent, then the reaction requires monitoring to determine the optimum column residence time before any significant secondary hydrolysis of γ-glutamylcysteine-mercaptoethanol has occurred, especially if a pH of about 8.5 or higher is employed. The effluent exiting the reaction column is pumped through a suitable pH controlled continuous flow mixing device and the pH of the mixture is adjusted to pH 12 with concentrated sodium hydroxide to stop the reaction.

The third stage of the continuous process for industrial production of GGC would involve the removal of the mercaptoethanol group and purification of the final product, or purification of the GGC-mercaptoethanol disulphide, removal of the mercaptoethanol group, and further purification of the GGC and crystallisation thereof, and may be performed in the same manner as described in the batch-wise process above.

g. Removal of Derivatizing or Solubilising Groups

The derivatizing groups attached to the reaction product can be removed and, depending on whether a disulphide reducing step is used, pure bis-γ-glutamylcystine, γ-glutamylcystine or γ-glutamylcysteine can be recovered by a variety of methods/chemistries as are well known in the art, including ion exchange chromatography, but most preferably by fractional crystallization.

i) Removal of Protecting/Solubilising Groups from the γ-Glutamyl Moiety

In the case of using a glutamic acid α,γ-alkyl ester as γ-glutamyl donor, the α-ester group is easily removed by saponification with 1 M sodium hydroxide and should occur simultaneously if a disulphide interchange reaction (adjustment of pH to 12) is used as the purification option.

ii) Removal of Protecting/Solubilising Groups From the Cysteinyl Moiety

Removal of protecting/solubilising groups from the cysteinyl moiety will be dependent on particular protecting/solubilising group used. In general, however, mixed disulphides can be either reduced to their corresponding thiols by chemical means (i.e. addition of excess thiol, or the use of a strong reducing agent such as sodium borohydride or the use of nascent hydrogen generated by an acid dissolving-metal reaction) (Jocelyn, P. C. Chemical reduction of disulfides. *Methods in Enzymology*, 1987. 143: p. 246-56) or by electrochemical means as previously described (Genders, J. D., et al. High yield methods for electrochemical preparation of cysteine and analogues. 1988. U.S. Pat. No. 5,106,463). An alternative option is to induce a disulphide interchange reaction by treatment with dilute NaOH. In the reaction scheme proposed all of the mixed (unsymmetrical) disulphides in the reaction mixture are converted to their symmetrical disulphides. The disulphide interchange reaction can be initiated by addition of a trace of thiol or by irradiation with UV light (Eager, J. E., et al. Photolysis and photo-oxidation of amino acids and peptides 0.6. A study of the initiation of disulphide interchange by light is irradiation. *Photochemistry and Photobiology*, 1963. 2(1): p. 25-37), and the reaction can be catalysed by selenol (Singh, R., et al. Selenols catalyze the interchange reactions of dithiols and disulfides in water. *Journal of Organic Chemistry*, 1991. 56(24): p. 6931-6933) or transition metal ions (Choi, J. S., et al. Synthesis of disulfides by copper—catalyzed disproportionation of thiols. *Journal of Organic Chemistry*, 1995. 60(11): p. 3266-3267).

Figure 7:
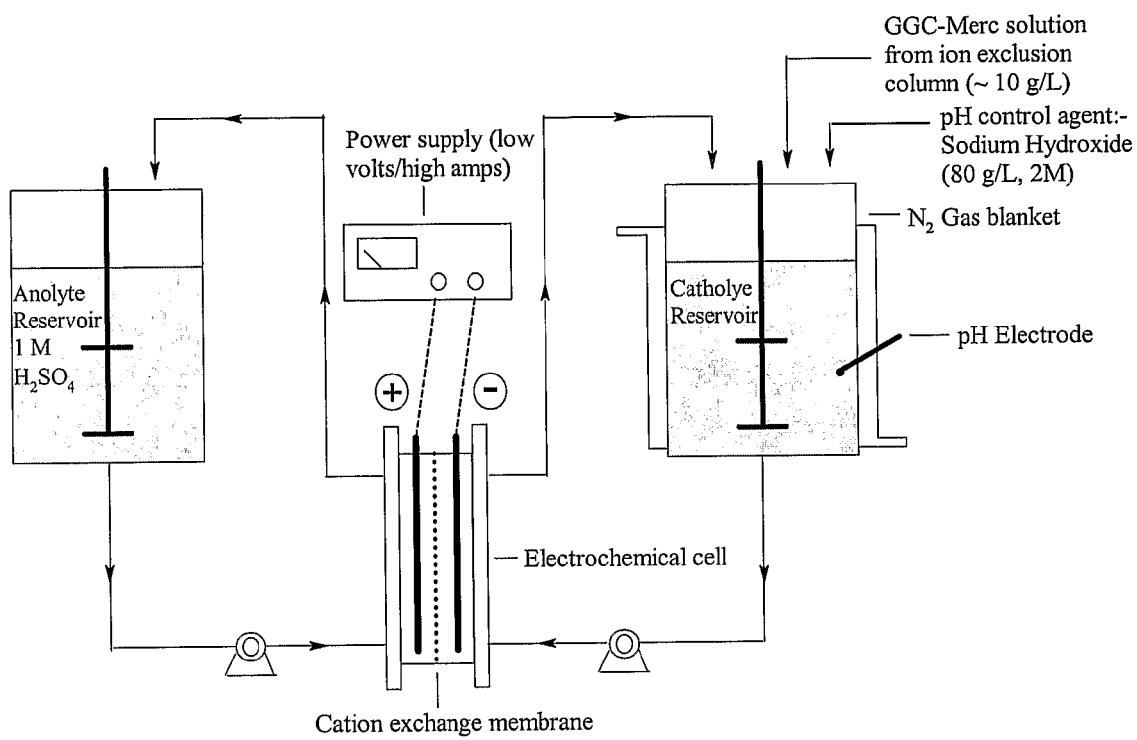
FIG. 7 is an illustration of apparatus for electrochemical reduction of GGC-mercaptoethanol disulphide.

The batch electrosynthesis of cysteine by the constant current reduction of cystine is an established industrial process with yields and selectivity for the process close to 100%. The general process for the electrochemical reduction of a disulphide such as cysteine is conducted in a parallel plate cell (See FIG. 7) with the cathode chamber (catholyte) and anode chamber (analyte) divided by an ion exchange membrane. Cell division prevents oxidation of either the disulphide or the thiol at the anode. The cathode material can be selected from several materials including Pb, Zn, Ag, stainless steel or graphite and is in contact with a solution containing the disulphide to be reduced. The anode material can be selected from several materials including Pt, DSA, platinised titanium or graphite and is in contact with a solution of sulphuric acid. On application of an electrical current the following reactions occur.

| | |
|---|---|
| R-S-S-R + 2H$^+$ + 2e$^-$ → 2R-SH | Cathode reaction |
| 2H$_2$O → O$_2$ + 4H$^+$ + 4e$^-$ | Anode reaction |

The process is operated in the batch recycle mode at 25° C. until all of the disulphides in the batch are reduced to the thiol form.

h. Isolation and/or Purification of the γ-glutamyl Derivative

After removal of protecting/solubilising groups the γ-glutamylcysteine or derivative thereof may be purified from the reaction mixture by fractional crystallization. Depending on which derivatives are used in the process, after the enzyme process the reaction mixture may contain a variety of contaminants such as; cystine, glutamic acid, glutamic acid γ-ester, disulphides (e.g. 2-hydroxyethyl disulfide) and inorganic salts. After the majority of water from the reaction mixture is removed by evaporation, cystine and glutamic acid are easily removed by crystallization due to their low aqueous solubility at pH 3 (0.1 and 8.6 g/L, respectively). Most low molecular weight disulphides are non-polar and as such can be removed by partitioning into an appropriate non-polar organic solvent (for example, ethyl acetate, butyl acetate, 1-butanol or 2-ethyl-1-hexanol). It is likely that the γ-glutamylcysteine or derivative thereof should have a high aqueous solubility (>50 g/L) and it is expected that the majority of the product can be precipitated by the addition of a water miscible organic solvent (e.g. ethanol, acetone). Depending on the purity of the precipitated product a final polishing step may be performed by ion exchange chromatography.

Alternative means of isolating/purifying the γ-glutamylcysteine or derivative thereof comprise ion exchange chromatography, ion exclusion chromatography (see, for example, Eisenbraun, A., "Separation of amino acids by ion exclusion", 1962, U.S. Pat. No. 3,045,026) and electrodialysis, if there is sufficient difference between the γ-glutamylcysteine or derivative thereof and the reactants (γ-glutamyl donor and cysteine derivative).

For example, a large difference in the isoelectric point (pI) exists between γ-glutamylcysteine-mercaptoethanol disulphide (GGC-Merc pI=3.0) and the substrates (Cys-Merc, pI=5.3 and GEE pI=5.8). This may allow purification systems based on ionic charge such as ion exchange chromatography, ion exclusion chromatography and electrodialysis to be readily exploited.

Where ion exchange, ion exclusion or electrodialysis methods can be exploited, these could be performed simultaneously with the enzyme reaction, allowing for increased product yield by effectively removing (or trapping) the product as it is formed and thereby driving the equilibrium towards product formation. As an example, instead of adding sodium hydroxide to the enzyme reaction to neutralize the acidic product GGC-Merc an anion exchange resin in the OH⁻ form could be added to both maintain the pH and selectively remove the reaction product. Similarly the enzyme reaction could be performed in an electrodialysis cell thereby facilitating continuous removal of GGC-Merc.

With GGC or GGC-Merc, ion exclusion chromatography is a technique of particular interest, as water may be used as the solvent/eluent, and GGC or GGC-Merc elute in the totally excluded volume of the cation exchange resin column at pH 5-7, whereas elution of Cys-Merc is delayed due to its slight positive charge at this pH, as is elution of glutamic acid γ-ethyl ester, which will have virtually no charge at this pH.

Metal ion affinity chromatography (IMAC) is another potential method that may be applicable to the purification of γ-glutamylcysteine or a derivative thereof. Several researchers have reported efficient separations of amino acids and dipeptides using copper$_{(II)}$ ions immobilized on resin bound iminodiacetic groups (for example, see: Belew and Porath, Immobilized metal ion affinity chromatography: effect of solute structure, ligand density and salt concentration on the retention of peptides, *Journal of Chromatography*, 1990, 516, 333-54; Shao and Liu, Preparation of chromatograph medium for separating amino acid and polypeptide and separating process thereof, 1997, Chinese patent No. 1163902).

Where a γ-glutamylcysteine derivative, such as γ-glutamylcysteine-mercaptoethanol disulphide is isolated/purified, this may require either chemical or electrochemical reduction to remove the derivatizing group (such as mercaptoethanol). Subsequent separation of the γ-glutamylcysteine from the released/contaminant compound (such as 2-mercaptoethanol) may then be required—this may be achieved by any of a number of techniques as known in the art, such as the techniques described above, including evaporation and differential crystallisation, or partitioning of the contaminant compound into an appropriate non-polar organic solvent (for example, ethyl acetate, butyl acetate, 1-butanol or 2-ethyl-1-hexanol), which technique has been found to be effective for removal of mercaptoethanol from γ-glutamylcysteine.

In an exemplary process of the invention, the preparation of a suitable γ-glutamyl derivative would be one of the first steps of the industrial production of GGC. For a 1000 L scale enzyme reaction, the preferable γ-glutamyl derivative, glutamic acid γ-ethyl ester may be synthesized by a couple of methods, amongst others, as described below.

In a first method, glutamic acid (15 kg) is suspended in anhydrous ethanol (150 L) containing dissolved hydrogen chloride gas (9 kg) and the mixture is stirred in a reaction vessel equipped with a cooling jacket thermostatted to 25° C. until all the solids have dissolved. The solution is diluted with water (250 L) and excess acid is neutralized by adding 50% sodium hydroxide solution. From the reaction mixture, ethanol can be removed by evaporation under reduced pressure and the volume lost is replaced by water (final volume 400 L). The final yield of glutamic acid γ-ethyl ester would be expected to be in the order of 17 kg.

In a second method, the glutamic acid γ-ethyl ester may be synthesised by the method described in U.S. Pat. No. 3,770,807 (1973). For example, glutamic acid (23 kg) may be solubilised in anhydrous ethanol (150 L) with concentrated sulphuric acid (98%, 18.7 kg, which also acts as the esterification catalyst) added dropwise and then reacted for 2 hours at 27° C. The reaction mixture is then cooled to 0° C. and an equimolar amount of sodium hydroxide dissolved in water (40% of the volume of ethanol) is added slowly to neutralize the acid. This results in crystallization of the sodium sulphate which is not soluble in 60% ethanol. The γ-glutamyl ester is soluble in 60% ethanol. The resulting filtrate can be concentrated by evaporation and finally crystallized by the addition of more than 80% ethanol. Crystallization of the ester may not be necessary as the ethanol can be distilled off, replaced by water, and used directly in the subsequent enzyme reaction. The final yield of glutamic acid γ-ethyl ester would be expected to be in the order of 17 to 18 kg. The preparation of a suitably soluble cysteine derivative would be another of the first steps of the industrial production of GGC. For a 1000 L scale enzyme reaction, the preferable cysteine derivative, cysteine-mercaptoethanol disulphide (Cys-Merc) can be synthesized by any suitable means, such as by use of a thiosulphinate intermediate or using copper ion air/$O_2$ oxidation of 2-mercaptoethanol or DTDE and cysteine or cysteine as described above.

For example, in the case of use of a thiosulphinate intermediate, 2-Hydroxyethyl disulphide (mercaptoethanol disulphide) (10 kg) is dissolved in water (100 L) in a reaction vessel equipped with a cooling jacket thermostatted to 20° C. Peracetic acid (9.8 kg) dissolved in 25% (w/v) acetic acid (100 L) is added slowly with constant stirring. After stirring for 3 hours, the solvent is removed by evaporation under reduced pressure. Water (200 L) is added to the resulting 2-hydroxyethyl thiolsulphinate and the pH adjusted to pH 6.5 with 50% sodium hydroxide. To a stirred solution of cysteine (14 kg) dissolved in water (200 L) and adjusted to pH 6.5, is added the 2-hydroxyethyl thiolsulphinate solution over 20 minutes. The reaction mixture is stirred overnight and any unreacted 2-hydroxyethyl thiolsulphinate is partitioned into ethyl acetate by continuous countercurrent extraction. The aqueous phase is then adjusted to pH 5.2 with 50% sodium hydroxide and any residual ethyl acetate solvent removed by evaporation under reduced pressure (final volume 400 L). The final yield of Cys-Merc would be expected to be in the order of 19 kg.

Alternatively, in the case of copper ion air/$O_2$ oxidation production of a Cys-mercaptoethanol intermediate, 2-Hydroxyethyl disulphide (10 kg) and cysteine (5.2 kg) may be dissolved in water (~210 L) and the pH of the solution adjusted to a pH of about 8.5 with sodium hydroxide, the temperature controlled to 37° C. and an aliquot (about 45 mL) of copper$_{(II)}$ chloride solution (100 mg/mL) added. The mixture is then vigorously aerated for about 18 hours with pH maintained at about pH 8.5. The copper ions in the resulting reaction mixture may be removed with a chelating resin with a high selectivity for copper$_{(II)}$ ions. The resulting reaction mixture will contain approximately 0.2M Cys-Merc and can either be used directly in a subsequent enzyme catalysed reaction for production of GGC or derivative thereof, or the Cys-Merc can be isolated by the addition of an equal volume of acetone and adjusting the pH of the reaction mixture to pH 5.2 with acetic acid, and the resulting crystalline material recovered by filtration or centrifugation and optionally washed and dried.

The preparation of an appropriate quantity of enzyme γ-glutamyltranspeptidase would be another first step in the industrial production of GGC. It is preferable to extract and purify γ-glutamyltranspeptidase from bovine milk by using low-cost procedures known in the art such as, for example, concentration by ultrafiltration, salting-out, solvent precipitation, and proteolytic digestion (to remove contaminating proteins) techniques, or combinations thereof. Solubilised γ-GT may be immobilized by suspending Eupergit C250L (Röhm GmbH & Co) epoxy activated resin beads (20 kg) in a solution comprising the γ-glutamyltranspeptidase and incubating the mixture for about 3 days at room temperature. Under ideal conditions the resin should contain a total of approximately 7,000,000 Units of γ-GT.

The second stage of the industrial production of GGC would involve the formation of the γ-glutamyl bond. The prepared 400 L aqueous solutions of the two derivatives of the amino acids are mixed together and the pH of the mixture adjusted to about pH 8.0 to about pH 9.0. Due to difficulties in controlling pH in a chromatography column, appropriate buffering may be required to maintain the pH at the desired level, or close to it, especially if a pH closer to 8.0 is used. The volume is adjusted to give a final concentration of γ-glutamic acid ethyl ester at approximately 18 g/L and Cys-Merc at 20 g/L (final volume approximately 1000 L). The prepared immobilized γ-GT enzyme resin beads are packed into a column equipped with a jacket thermostatted to 37° C. and the above mixture pumped through the column at a rate in which the effluent contains at least 10 g/L of γ-glutamylcysteine-mercaptoethanol disulphide (30% yield on either substrates). The immobilized column should be able to be reused for numerous batches without any appreciable loss in γ-GT activity.

The third stage of the industrial production of GGC would involve the removal of the mercaptoethanol group and then purification of the GGC, or isolation of the GGC-mercaptoethanol disulphide, removal of the mercaptoethanol group, and further purification of the GGC.

The GGC or GGC-Merc may be isolated or purified from reactants (γ-glutamyl donor, cysteine derivative and by-products, such as 5-oxopyrrolidone-2-carboxylic acid) or from derivatives released from the γ-glutamylcysteine derivative by any suitable means, some of which have already been described above. Particularly relevant methods which may be applicable to an industrial process comprise solvent partitioning, fractional crystallisation, ion-exchange chromatography (which may be performed in a column, but not necessarily), ion-exclusion chromatography, electrodialysis or metal ion affinity chromatography.

Particularly convenient for industrial purification of GGC or GGC-mercaptoethanol disulphide would be ion-exclusion chromatography, in which the GGC or GGC-Merc are eluted, substantially free of cysteine-mercaptoethanol, glutamic acid γ-ethyl ester mixed disulphide and by-product in the totally excluded, or void volume of a column packed with a suitable cation exchanger (about pH 5-7). The reactants and by-products are eluted in delayed fractions. Also, to increase the number of separations in a given period the subsequent aliquots of enzyme reaction mixture could be increased by injection before the last peak of the previous injection had eluted.

Mercaptoethanol groups can be cleaved from GGC-Merc, either before or after isolation/purification, and the released GGC purified or further purified by any suitable means, some of which have been described above.

For example, as described above, one sequence of steps from formation of GGC-mercaptoethanol disulphide to substantially pure GGC, which may be particularly attractive for implementation in an industrial process comprises electrochemical reduction of GGC-mercaptoethanol disulphide to cleave the mercaptoethanol group, followed by removal of mercaptoethanol from the reaction mixture. Mercaptoethanol removal may be achieved by partitioning with a non-polar solvent and the purified GGC precipitated by ethanol addition (to greater than 80% v/v).

In another means for cleaving the mercaptoethanol group and purifying the released GGC, a disulphide interchange reaction is initiated by adjusting the pH of the reaction mixture to pH 12 with 50% sodium hydroxide and the reaction is monitored by HPLC analysis until no mixed disulphide is present (several hours). At the same time, water can be removed from the reaction mixture by evaporation under reduced pressure until the volume is reduced by half (500 L). The pH of the reaction mixture is then adjusted to pH 3 with glacial acetic acid, which should be accompanied by the precipitation of unreacted cystine, which can be removed by filtration. The by-product 2-hydroxyethyl disulphide is partitioned into ethyl acetate by continuous counter current extraction of the filtrate and the volume of the resulting aqueous phase can be further reduced by evaporation under reduced pressure. The purification of bis-γ-glutamylcystine can be effected by fractional crystallization, followed by ion exchange chromatography as a final polishing step. The final yield of bis-γ-glutamylcystine would be expected to be in the order of 15 kg.

Uses of γ-Glutamylcysteine or Other Compounds Comprising an α,γ Amide Linkage Between a Cysteine Moiety and a Glutamic Acid Moiety Obtained by the Processes of the Invention Although the processes of the present invention may be used to prepare a wide range of compounds comprising an α,γ amide linkage between cysteine and glutamic acid moieties, particularly contemplated by the present invention are γ-glutamylcysteine, its oxidised dimer bis-γ-glutamylcystine, γ-glutamylcystine and γ-glutamylcysteine α-glutamyl alkyl esters (esters have been shown to be transported across cell membranes even more effectively than γ-glutamylcysteine, with a demonstrable improvement in antioxidant effect).

The present invention thus also relates to a compound selected from γ-glutamylcysteine, bis-γ-glutamylcystine, γ-glutamylcystine and other compounds comprising α,γ amide linkages between cysteine and glutamic acid moieties, such as γ-glutamylcysteine α-glutamyl alkyl esters, obtained by processes of the invention. The compound may be purified to a desired degree.

γ-Glutamylcysteine, bis-γ-glutamylcystine, γ-glutamylcystine or a γ-glutamylcysteine α-glutamyl alkyl ester may be used in a wide variety of applications as a catalyst, reactant or reductant/antioxidant. Fields of application include, but are not restricted to personal health care, pharmaceuticals, nutraceuticals, cosmetics, food (including bakery and fermentation technology), agriculture (including animal feeds) and fermentation media. For pharmaceutical purposes the γ-glutamylcysteine is preferably provided as a purified compound, typically greater than 60% pure, more typically greater than 70% pure, more typically greater than 80% pure, even more typically greater than 90% pure, and more preferably greater than 95% pure.

Thus, the present invention also relates to a personal health care composition comprising γ-glutamylcysteine, bis-γ-glutamylcystine, γ-glutamylcystine or a γ-glutamylcysteine α-glutamyl alkyl ester obtained by the process of the invention and a pharmaceutically or topically acceptable carrier.

The present invention also relates to a pharmaceutical composition comprising γ-glutamylcysteine, bis-γ-glutamylcystine, γ-glutamylcystine or a γ-glutamylcysteine α-glutamyl alkyl ester obtained by the process of the invention and a pharmaceutically acceptable carrier. Such pharmaceutical compositions may be used in the treatment of, for example, cancer, cardiovascular disease (such as atherosclerosis), oxidative damage to tissue (such as aging, or progressive protein oxidation in the eye lens), respiratory distress syndrome, toxicology, AIDS, and liver disease.

The present invention also relates to a food or nutraceutical composition comprising γ-glutamylcysteine, bis-γ-glutamylcystine, γ-glutamylcystine or a γ-glutamylcysteine γ-glutamyl alkyl ester obtained by the process of the invention optionally in combination with one or more food components. The food/nutraceutical composition may be to selected from liquids, semi-solids and solids.

The present invention also relates to a dough or bread improving composition comprising γ-glutamylcysteine, bis-γ-glutamylcystine, γ-glutamylcystine or a γ-glutamylcysteine α-glutamyl alkyl ester obtained by the process of the invention and a suitable carrier. The carrier may be selected from a wide variety of bakery acceptable ingredients, including flour and/or sugar and the composition may also include other bread improving ingredients such as enzymes (including cellulases, glucanases, amylases, xylanases, arabinoxylanases, dextrinases, maltases, etc.). The composition may be in the form of a powder, granulate or liquid.

The present invention also relates to an animal feed additive comprising γ-glutamylcysteine, bis-γ-glutamylcystine, γ-glutamylcystine or a γ-glutamylcysteine α-glutamyl alkyl ester obtained by the process of the invention and a suitable carrier. The carrier may be selected from a wide variety of acceptable animal feed ingredients, such as flour (including wheat, corn or soy), and the composition may also include other animal feed additives including those which improve the digestibility of the food such as enzymes (including cellulases, glucanases, amylases, xylanases, arabinoxylanases, dextrinases, maltases, etc.). The composition may be in the form of a powder, granulate or liquid.

The present invention also relates to an animal health care composition comprising γ-glutamylcysteine, bis-γglutamylcystine, γ-glutamylcystine or a γ-glutamylcysteine α-glutamyl alkyl ester obtained by the process of the invention and a veterinary acceptable carrier.

The present invention also relates to a method for preventing oxidative damage in the circulation or tissues of a mammal, said method comprising administering to said mammal an effective amount of a composition comprising γ-glutamylcysteine, bis-γ-glutamylcystine, γ-glutamylcystine or a γ-glutamylcysteine α-glutamyl alkyl ester obtained by the process of the invention.

The present invention also relates to a method of protecting a food product from oxidative deterioration comprising adding to said food product an effective amount of γ-glutamylcysteine, bis-γ-glutamylcystine, γ-glutamylcystine or a γ-glutamylcysteine α-glutamyl alkyl ester obtained by the process of the invention or a composition comprising it. Food products prepared by said method are also provided. The food product may be liquid, semi-solid or solid.

The present invention also relates to a method of preparing a dough comprising combining dough components with an effective amount of γ-glutamylcysteine, bis-γ-glutamylcystine, γ-glutamylcystine or a γ-glutamylcysteine α-glutamyl alkyl ester obtained by the process of the invention. Doughs prepared by this method, or baked products derived therefrom are also provided.

Preferred forms of the present invention will now be described, by way of example only, with reference to the following examples, including comparative data, and which are not to be taken to be limiting to the scope or spirit of the invention in any way.

EXAMPLES

Example 1

Materials and Methods 1.1 HPLC Sample Preparation

Acid stopped enzyme reaction mixture (100 μL) was diluted into 0.1 M $K_2HPO_4$ (900 μL) and an aliquot (250 μL) dispensed into an Eppendorf tube containing 0.2 M mercaptoethanol in the same buffer (250 μL). The tube was incubated at 37° C. for 20 minutes to reduce all disulphides, and excess mercaptoethanol was removed by extraction with 3 aliquots of ethyl acetate (750 μL). The sample was diluted appropriately in HPLC mobile phase and stored at 4° C. ready for injection onto the HPLC.

1.2 Thiol Determination Using HPLC

Thiols were separated using a Shimadzu (Class VP) HPLC system with an Alltima (Alltech) C18, 5 μm, (250×4.6 mm) column (P/N 88057). Isocratic elution was performed with a mobile phase consisting of 0.1 M potassium dihydrogen phosphate, 0.35% acetonitrile (v/v) adjusted to pH 3.0 with 85% (w/v) phosphoric acid at a flow rate of 1 ml/min. Thiols were measured by electrochemical detection with a Coulochem II (ESA, Bedford, Mass.) detector set at +700 mV. GGC standard solutions were prepared in mobile phase at a concentration between 4 to 25 μM, with typically 20 μL of sample or standard injected onto the HPLC system.

1.3 γ-Glutamyltranspeptidases (γ-GTs)

The γ-GT used in many of the following examples was a crude preparation from bovine kidney, as the tissue containing the highest concentration of γ-GT is the kidney it is a commonly used source of γ-GT. However, bovine milk has been identified as an excellent source of γ-GT as it is found in relatively high concentration (~4 U/mL), and this enzyme has been used in those examples where specified. A high yielding purification of γ-GT from bovine milk, suitable for industrial production has also been prepared by papain digestion to remove contaminating proteins and an acetone precipitation (equal volume of acetone added) followed by lyophilization. The final lyophilized product contained 23.3 U/g of γ-GT at a yield of 30% on the initial activity and with a 167-fold purification factor. Preliminary testing in reaction conditions which is the milk γ-GT indicated no significant difference in activity and GGC yield to that of the kidney sourced enzyme. An example of the purification may be as follows: milk whey is initially concentrated 10-fold by ultrafiltration and the majority of contaminating proteins removed by digestion with a suitable protease, preferably papain. After digestion at 37° C. for several hours, the mixture is diafiltered against water and concentrated 2-fold. γ-GT in the concentrate is precipitated by the addition of ammonium sulphate (40% w/v) and solids formed are collected by centrifugation. The enzyme precipitate is resuspended in 0.5 M potassium phosphate buffer at pH 8.5 containing 1% Triton X100, and any remaining undissolved solids are removed by filtration. γ-GT in the concentrate is precipitated by the addition of an equal volume of acetone and the solids formed are collected by centrifugation. The solids may then be lyophilized to yield a dry powder preferably containing at least 20 U/mg of γ-GT.

An alternative process for purification of γ-GT from cow's milk has been developed as follows:

To fresh unpasteurized cow's milk (10 L, containing approximately 3 U/mL of γ-glutamyltranspeptidase) at 4° C. was added Triton X-100 (10 g) with strong mixing. The major protein content of milk (casein, 80%) can be precipitated by any of the three following methods.

The conventional method (No. 1) results in usually 50% loss of the milk enzyme activity. The other two methods (No. 2 & 3) usually result in no more than 10% loss. Method No. 1 is given here as it represents the first step in commercial cheese making from which whey is a waste product.

1. At 20° C. the pH of the 1% Triton X-100 in milk (10 L) was adjusted to 4.5 by the slow addition of a 50% solution of acetic acid with strong mixing. The curds (casein) were removed by filtration through a fine nylon mesh and the whey collected for further processing 2. A solution of chitosan (4.5 L, 1% in 10 mM sodium acetate at pH 5.9) was added in to the 1% Triton X-100 in milk (10 L) with strong mixing. The curds (casein) were removed by filtration through a fine nylon mesh and the whey collected for further processing 3. Ethanol (4.5 L) cooled to 4° C. was added slowly to the 1% Triton X-100 in milk (10 L) at 4° C. with strong mixing. The curds (casein) were removed by filtration through a fine nylon mesh and the whey collected for further processing.

The following process can be used for whey prepared from any of the above three methods. In this example the whey prepared by method No. 2 was used. The pH of the resulting whey was adjusted to pH 7.4 with 1 M sodium hydroxide and 1 M calcium chloride (100 mL), added to effect precipitation of contaminating and potentially membrane fouling lipoproteins. The solution was incubated for 4 hours at 30° C. and the solids removed by centrifugation at 5,000 g for 15 min. The supernatant was clarified by cross flow filtration through a membrane filter (Sartorius, Hydrosart 0.2 μm, 0.6 m²) and then concentrated by cross flow ultrafiltration (Sartorius, Ultrasart 10,000 Mwt cut off, 0.7 m²) to 10% of the initial volume. The retentate was washed by diafiltration against 50 mM triethanolamine buffer (20 L) and repeated twice, each time concentrating down to 10% of the initial volume. To the retentate (1.5 L) was added disodium EDTA (1 g/L), cysteine (0.5 g/L) and papain (3000 U) and the pH adjusted to pH 5.0 by the addition of 1 M hydrochloric acid. The contaminating proteins were hydrolysed by incubation at 37° C. for 1 hr. The pH was then adjusted to pH 7.0 by the addition of 1 M sodium hydroxide and incubated at 37° C. for 1 hr. The pH was then adjusted to pH 5.0 by the addition of 1 M sodium hydroxide and incubated at 37° C. a further hour. The hydroslyate was cooled to 15° C. and ammonium chloride added to 40% saturation. The contaminating proteins solids were removed by centrifugation at 8,000 g for 10 min and the supernatant made to 60% saturation ammonium chloride. The resulting solid γ-glutamyltranspeptidase was collected by centrifugation at 8,000 g for 10 min, resuspended in water (200 mL) and stored at −20° C. or freeze dried. The concentrate contained 130 U/mL of γ-glutamyltranspeptidase (87% yield) at a specific activity of 8 U/mg total protein (protein determined as per (Peterson, Simplification of Protein Assay Method of Lowry Et Al—Which Is More Generally Applicable, *Analytical Biochemistry,* 1977, 83, 346-56) modification of the Lowry protein assay).

1.4 γ-Glutamyltranspeptidase Assay

Reaction samples were diluted in 0.1 M Tris buffer (pH 8.0) to give a final γ-glutamyltranspeptidase concentration within the range of 0.02-0.44 units/mL in the diluted samples. Samples within this range of enzyme concentrations gave corrected absorbance readings (410 nm) from 0.060-1.300 absorbance units, which was identified as being the linear range of the γ-glutamyl-p-nitroanilide assay (data not shown). An aliquot (100 μL) was added to the reaction mixture (900 μL) containing 2 mM L-γ-glutamyl-p-nitroanilide substrate, 0.1 M glycylglycine, 10 mM sodium chloride and 0.1 M Tris buffer adjusted to pH 8.0 and incubated at 37° C. for 10 minutes. The reaction was quenched by the addition of 1.5 N acetic acid (2.0 mL) and the absorbance at 410 nm measured ($\epsilon_{410\,nm}$ for p-nitroaniline is 8800 $M^{-1}$ $cm^{-1}$). One unit of γ-glutamyltranspeptidase was defined as the amount of enzyme which liberates one μmole of p-nitroanilide per minute at 37° C. at pH 8.0. The γ-glutamyltranspeptidase supplied by Sigma Chemical Co. used in the study was a crude lyophilized extracted from bovine kidney (fraction 1) as described in (Szewczuk, A. and T. Baranowski, Purification and Properties of γ-Glutamyltranspeptidase from Beef Kidney. *Biochimische Zeitschrift,* 1963. 338(338): p. 317-329)—the pH optimum of the purified enzyme between pH 8.8-9.0. The activity of the enzyme was determined to be 7.2 U/mg solids.

1.5 Synthesis of γ-Glutamylmethylamide

Adapted from (Lichtenstein, N. Preparation of γ-alkylamides of glutamic acid. *Journal of the American Chemical Society.* 1942. 64: p. 1021-1022)

To an aqueous solution of 17% methylamine (30 mL) is dissolved pyrrolidinecarboxylic acid (2.5 g) and incubated in a sealed bottle at 37° C. for 10 days. The reaction mixture is transferred into a crystallizing dish, placed in a desiccator over sulphuric acid and concentrated for one day under reduced pressure. The resulting syrup is rubbed with ethanol (25 mL) and allowed to stand at 4° C. overnight. The resulting crystalline precipitate is collected by filtration in a Buchner funnel and washed with cold ethanol. The filter cake is dried under reduced pressure over silica gel in a desiccator.

1.6 Synthesis of Cysteine-Mercaptoethanol Mixed Disulphide 1.6.1a Synthesis of Cystine Thiosulphonate Cystine (9.6 g) was placed in a 500 mL round bottom flask equipped with a magnetic stirrer, thermometer, and formic acid (88%; 222 mL) was added with mixing. The flask was cooled by immersion in an ice bath when necessary to maintain the temperature of the solution at 20° C. Concentrated hydrochloric acid (36%; 8 mL) was added slowly, followed by the slow addition of hydrogen peroxide (30%; 10 mL) with constant stirring. After stirring for 2.5 hours at 20° C., the solvent was removed under reduced pressure on a rotary evaporator with the water bath set at 50° C. Water (100 mL) was added to the resulting thick syrup, followed by the addition of ammonium hydroxide (26%; 10 mL) to adjust the pH to pH 3.5. The flask was allowed to stand overnight at 4° C. overnight and the resulting precipitate was collected by filtration in a Buchner funnel and washed with ice-cold water (30 mL). The filter cake was dried under reduced pressure over silica gel in a desiccator.

1.6.1b Synthesis of Cysteine-Mercaptoethanol Mixed Disulphide (Cys-Merc)

A solution of mercaptoethanol (1.02 g; 13 mmol) in water (25 mL) was adjusted to pH 6.3 with 2 M sodium hydroxide. A solution of cystine thiosulphonate (4.17 g; 16.3 mmol) in water (70 mL) adjusted to pH 6.3 with 2 M sodium hydroxide was added over a period of 10 minutes, with constant stirring. The reaction mixture was stirred overnight at room temperature and then extracted with 3×50 mL portions of ethyl acetate to remove unreacted mercaptoethanol. The aqueous phase was then adjusted to pH 5.2 with 2 M sodium hydroxide and the solvent removed under reduced pressure on a rotary evaporator with the water bath set at 60° C. The resulting residue was dissolved in hot water (50 mL) and clarified by filtration through Whatman No. 1 paper in a Buchner funnel. Warm isopropyl alcohol (approx. 100 mL) was added to the filtrate until a persistent turbidity formed. The mixture was allowed to stand overnight at 4° C. and the resulting precipitate was collected by filtration in a Buchner funnel and washed with cold 30% (v/v) isopropyl alcohol (30 mL). The filter cake was dried under reduced pressure over silica gel in a desiccator.

Apart from the synthesis of cysteine-mercaptoethanol via the cystine thiosulphonate intermediate as described above, several alternatives are possible and are described below.

1.6.2 Alternative synthesis of cysteine-mercaptoethanol disulfide—adapted from (Schoberl, A. Synthese und reaktions weise von unsymmetrischen disulfiden 0.6. Aminocarbonsauren und haarkeration mit unsymmetrisch eingebauten disulfidaustausches. *Annalen Der Chemie-Justus Liebig*, 1958. 617(1-3): p. 71-88) and Nagasawa et al ("Mixed disulfides of L-cysteine and its derivatives with 2-mercaptoethanol" *Organic Preparations and Procedures International (Briefs)*, 1996. 28(2): p. 237-241).

2-Hydroxyethyl disulfide (mercaptoethanol disulfide) (7.7 g) is dissolved in methanol (100 mL) in a 500 mL round bottom flask equipped with a magnetic stirrer and thermometer. The flask is cooled by immersion in an ice bath when necessary to maintain the temperature of the solution at 20° C. Peracetic acid (3.8 g) dissolved in 25% (w/v) acetic acid (100 ml) is added slowly with constant stirring. After stirring for 3 hours, the solvent is removed under reduced pressure on a rotary evaporator with the water bath set at 60° C. Water (100 mL) is added to the resulting thick syrup of 2-hydroxyethyl thiolsulphinate and the pH adjusted to 6.5 with 2M sodium hydroxide. To a stirred solution of cysteine (10 g) in water (150 mL), adjusted to pH 6.5, is added the 2-hydroxyethylthiolsulphinate solution over 10 minutes. The reaction mixture is stirred overnight and then extracted with 3×100 mL portions of ethyl acetate to remove unreacted 2-hydroxyethyl thiolsulphinate. The aqueous phase is then adjusted to pH 5.2 with 2M sodium hydroxide and the solvent removed under reduced pressure on a rotary evaporator with the water bath set at 60° C. The resulting residue is dissolved in hot water (200 mL) and clarified by filtration through Whatman No. 1 paper in a Buchner funnel. Isopropyl alcohol (approx. 300 mL) is added to the filtrate until a persistent turbidity forms. The mixture is allowed to stand overnight at 4° C. and the resulting precipitate is collected by filtration in a Buchner funnel and washed with cold 30% (v/v) isopropyl alcohol (30 mL). The filter cake is dried under reduced pressure over silica gel in a desiccator. The mercaptoethanol group is easily removed under standard reducing conditions as described by Jocelyn, P. C. (Jocelyn, P. C., Chemical reduction of disulfides. *Methods in Enzymology.*, 1987.143: p. 246-56).

1.6.3a Alternative synthesis of cysteine-mercaptoethanol disulfide—Synthesis of cystine thiolsulphinate (S-monoxide)—adapted from (Walti, M. Synthesis of isomers of mono- and di-hydroxy-analogues of cystine and comparison with metabolites excreted in urine. *Journal of the Chemical Society C-Organic*, 1971. (12): p. 2326-&)

Cystine (10 g) is dissolved in 2N sulphuric acid (100 mL) in a 500 mL round bottom flask equipped with a magnetic stirrer and thermometer. The flask is cooled by immersion in an ice bath to maintain the temperature of the solution at 0° C. A solution of 1M peracetic acid (83 mL) dissolved in acetic acid (100 ml) is added slowly with constant stirring. The mixture is kept at 0° C. overnight and then adjusted to pH 4 with cold pyridine. Ethanol (500 ml) is added to the mixture and the resulting precipitate is collected by filtration in a Buchner funnel and washed first with methanol (100 mL) and then ether (50 mL). The filter cake is dried under reduced pressure over silica gel in a desiccator. The cystine thiolsulphinate produced can be used in the following synthesis to prepare the mixed disulphide with mercaptoethanol.

1.6.3b Alternative synthesis of cysteine-mercaptoethanol disulfide—adapted from (Walti, M. Synthesis of isomers of mono- and di-hydroxy-analogues of cystine and comparison with metabolites excreted in urine. *Journal of the Chemical Society C-Organic*, 1971. (12): p. 2326-&) and Nagasawa et al ("Mixed disulfides of L-cysteine and its derivatives with 2-mercaptoethanol" *Organic Preparations and Procedures International (Briefs)*, 1996. 28(2): p. 237-241).

A solution of mercaptoethanol (3.9 g; 50 mmol) in water (25 mL) is adjusted to pH 6.3 with 2M sodium hydroxide. A solution of cystine thiolsulphinate as prepared above (6.5 g; 25 mmol) dissolved in water (100 mL), adjusted to pH 6.3 with 2M sodium hydroxide is added over a period of 10 minutes, with constant stirring. The reaction mixture is stirred overnight at room temperature and then extracted with 3×50 mL portions of ethyl acetate to remove unreacted mercaptoethanol. The reaction product is worked up as described in the above example: the aqueous phase is then adjusted to pH 5.2 with 2M sodium hydroxide and the solvent removed under reduced pressure on a rotary evaporator with the water bath set at 60° C. The resulting residue is dissolved in hot water (200 mL) and clarified by filtration through Whatman No. 1 paper in a Buchner funnel. Isopropyl alcohol (approx. 300 mL) is added to the filtrate until a persistent turbidity forms. The mixture is allowed to stand overnight at 4° C. and the resulting precipitate is collected by filtration in a Buchner funnel and washed with cold 30% (v/v) isopropyl alcohol (30 mL). The filter cake is dried under reduced pressure over silica gel in a desiccator.

1.6.3c Alternative Synthesis of Cysteine-Mercaptoethanol Disulfide

2-Hydroxyethyl disulphide (2-mercaptoethanol disulphide) (23.3 g) and cysteine (12.1 g) were dissolved in water (500 mL) in an Erlenmeyer flask and the pH of the solution was adjusted to pH 8.5 with sodium hydroxide (2M). The flask was placed in a water bath thermostatted at 37° C. and an aliquot (100 μL) of copper$_{(II)}$ chloride solution (100 mg/mL) added. The mixture was vigorously aerated by bubbling in air through a stainless steel frit for 18 hours. Over the reaction period the pH was occasionally checked and adjusted to pH 8.5 if necessary by the addition of dilute hydrochloric acid. The concentrations of thiols in the reaction mixture were conveniently monitored spectrophotometrically using Ellman's reagent. The reaction was considered complete when no yellow colour formation was observed when an aliquot of reaction mixture is added to Ellman's reagent, thus indicating that all thiols had been oxidized to disulphide. The copper ions in the resulting reaction mixture were removed by passage through a column (1×3 cm) of chelating resin with a high selectivity for copper$_{(II)}$ ions such as Chelex 100 resin (Bio-Rad). The resulting reaction mixture contains 0.2M Cys-Merc and can either be used directly in a subsequent enzyme catalysed reaction for production of GGC or derivative thereof, or Cys-Merc can be isolated by the addition of an equal volume of acetone and adjusting the pH of the reaction mixture to pH 5.2 with acetic acid. Spontaneous crystallization occurs and the mixture is allowed to stand overnight at 4° C. The resulting crystalline suspension was collected by filtration in a Buchner funnel, washed with cold 50% acetone and dried under reduced pressure over silica gel in a dessicator. Upon drying, Cys-Merc (17.9 g, 91% of the theoretical yield), was obtained.

1.7 Synthesis of Cystine Dimethyl Ester Dihydrochloride (CDME)

A stream of dry hydrogen chloride gas was sparged rapidly into a suspension of cystine (10 g) in anhydrous methanol (50 mL) and agitated with a magnetic stirrer. After all the cystine had dissolved the warm solution was cooled in an ice bath, and sparging of HCl continued to saturation at 0-5° C. The reaction mixture was protected from atmospheric moisture with a calcium chloride drying tube and allowed to stand at room temperature for 3 hours. Solvent was removed from the reaction mixture under reduced pressure on a rotary evaporator with the water bath set at 50° C. An aliquot of methanol (50 mL) was added to the resulting syrup and then concentration by rotary evaporation repeated. To the dry syrupy residue was added anhydrous ether (20 mL) resulting in spontaneous crystallization. The mixture was allowed to stand overnight at 4° C. and the resulting crystalline suspension was collected by filtration in a buchner funnel and washed with cold anhydrous ether (30 mL). The filter cake was dried under reduced pressure over potassium hydroxide pellets in a desiccator.

1.8 Synthesis of Other Water-Soluble Cyst(e)ine Derivatives 1.8.1 S-Acetamidoalkyl Derivatives Synthesis of S-Acetamidomethylcysteine hydrochloride. Adapted from (Milkowski, J. D. Thiol protection with the acetamidomethyl group—S-acetamidomethyl-L-cysteine hydrochloride. *Organic Syntheses*, 1988. 5: p. 5-8)

In a 1-litre round-bottomed flask, N-(hydroxymethyl)acetamide (127 g), and cysteine hydrochloride monohydrate (228 g) are dissolved in water (350 mL). The resulting solution is swirled and cooled in an ice bath as concentrated hydrochloric acid (50 mL) is slowly added. The flask is flushed with nitrogen, capped with a nitrogen-filled balloon, and allowed to stand for 1-2 days at room temperature. The progress of the reaction is monitored by TLC, which can be performed on silica gel 60F-254 precoated plates (Merck) with a 10:2:3 (v/v/v) solution of 1-butanol, acetic acid, and water as developing solvent. The spots can be visualized with UV light or using ninhydrin. When cysteine hydrochloride is no longer detectable, the solution is evaporated under reduced pressure at a bath temperature of about 40° C. The remaining solids are suspended in a small amount of absolute ethanol, and the mixture again carefully evaporated to avoid bumping. The entrainment procedure with absolute ethanol is repeated several times to remove traces of water. The dry solids are dissolved in the minimum amount of methanol and anhydrous diethyl ether added until the cloud point is reached. The cloudy solution is allowed to stand at 4° C. for 1 week, during which the crystalline mass is broken up several times. The white crystalline product is collected by filtration in a Buchner funnel and washed with cold ether. The filter cake is dried under reduced pressure over silica gel in a desiccator. The S-acetamidomethylcysteine derivative can be used directly as an acceptor in the transpeptidation reaction and the S-acetamidomethyl can be removed by a variety of methods including reaction with iodine or an $HG_{(II)}$ salt.

1.8.2 S-Sulphocysteine

Synthesis of S-sulphocysteine sodium salt dihydrate. Adapted from (Maugras, I. Peptide-synthesis using novel S-sulfocysteine derivatives. *International Journal of Peptide and Protein Research*, 1995. 45(2): p. 152-156)

To a solution of cysteine hydrochloride dihydrate (10.54 g) in water (100 mL) is added successively, 1M sodium hydroxide (60 mL) and sodium tetrathionate dihydrate (18.38 g). After 1 hour stirring at room temperature the reaction is complete (TLC monitoring, as described above). The reaction mixture is concentrated under reduced pressure on a rotary evaporator to half its volume and left at 4° C. overnight. The resulting solids are removed by filtration and discarded. After standing for several hours at 4° C. the sulfur that had precipitated from the filtrate is removed by filtration. The volume of the filtrate is reduced to 100 mL on a rotary evaporator under reduced pressure, and ethanol is added (800 mL). The mixture is allowed to stand overnight at 4° C. and the resulting precipitate is collected by filtration in a Buchner funnel and washed with cold 70% (w/v) ethanol. The filter cake is dried under reduced pressure over silica gel in a desiccator. The S-sulphocysteine derivative can be used either directly as an acceptor in the transpeptidation reaction or used to synthesize mixed disulphides of cysteine by reaction with the desired thiol as described by Stapleton (Stapleton, I. W. Amino acids and peptides 0.9. Some unsymmetrical disulphides derived from cysteine. *Australian Journal of Chemistry*, 1962. 15(3): p. 570-&). The S-sulpho group is easily removed under standard reducing conditions as described by Jocelyn, P. C. (Jocelyn, P. C., Chemical reduction of disulfides. *Methods in Enzymology.*, 1987. 143: p. 246-56).

1.8.3 Alkyl Esters of Cystine

For the synthesis of cystine dimethyl ester, the following procedure may be used, optionally scaled up. A suspension of cystine (20 g) in methanol (300 mL) under reflux is constantly bubbled through with dry hydrogen chloride gas for 2 hours. After an additional hour at room temperature the reaction mixture is concentrated on a rotary evaporator under reduced pressure, methanol (50 mL) is added and the evaporation to dryness repeated. The dry residue is diluted with ether (50 mL), allowed to stand overnight at 4° C., resulting in a crystalline suspension which can be collected by filtration in a buchner funnel, followed by washing with ether. The filter cake is then dried under reduced pressure over silica and sodium hydroxide pellets in a desiccator.

Synthesis of the monomethyl ester of cystine may be performed by a similar route by using only half the molar equivalent of methanol, saturating the cystine/methanol in a chloroform solution with hydrogen chloride gas and heating to a gentle reflux for 1 hour and then cooling to room temperature for approximately 1 hour. The reaction product is worked up as described in the above example.

1.8.4 S-Alkoxycarbonylsulphenyl Derivative

Synthesis of S-Methoxycarbonylsulphenylcysteine hydrochloride. Adapted from (Rietman, B. H. A facile method for the preparation of S-(alkylsulfenyl)cysteines. *Synthetic Communications.* 1994. 24(9): p. 1323-1332)

To a solution of cysteine hydrochloride (4.46 g) in anhydrous methanol (38 mL) is bubbled through shortly with hydrogen chloride. The mixture is slowly dropped into a solution of methoxycarbonylsulphenyl chloride (5 ml) in methanol (40 mL) and magnetically stirred at 0° C. After 1 hour stirring the reaction is complete and the solvent is removed on a rotary evaporator under reduced pressure. The resulting residue is collected by filtration in a Buchner funnel and washed with ether. The filter cake is dried under reduced pressure over silica gel in a desiccator. The S-methoxycarbonylsulphenylcysteine derivative can be used either directly as an acceptor in the transpeptidation reaction or used to synthesize mixed disulphides of cysteine by reaction with the desired thiol as described by Brois and Rietman (Brois, S. J., et al. A new pathway to unsymmetrical disulfides. The thiol-induced fragmentation of sulfenyl thiocarbonates. *Journal of the American Chemical Society.* 1970. 92(26): p. 7629) and (Rietman, B. H. A facile method for the preparation of S-(alkylsulfenyl)cysteines. *Synthetic Communications.* 1994. 24(9): p. 1323-1332). The S-Methoxycarbonylsulphenyl group is easily removed under standard reducing conditions as described by Jocelyn, P. C. (Jocelyn, P. C., Chemical reduction of disulfides. *Methods in Enzymology.* 1987. 143: p. 246-56).

1.8.5 S-Acetylcysteine

Synthesis of S-Acetylcysteine. Adapted from (Galzigna, L., et al. S-acetyl-glutathione and S-phenylacetyl-glutathione as glutathione precursors in rat plasma and tissue preparations. *Enzyme & Protein* 1994. 48(2): p. 98-104)

While stirring under a nitrogen blanket, acetyl chloride (9.57 g) is added drop wise to a solution of cysteine (6.09 g) in trifluoroacetic acid (200 ml) at room temperature. The reaction mixture is heated to 40° C. and after about 20 minutes water (5 ml) is added to stop the reaction. After another 20 minutes incubation at 40° C., the solvent is removed on a rotary evaporator under reduced pressure, and the resulting oil is dissolved in ethyl acetate. The mixture is allowed to stand overnight at 4° C. and the resulting precipitate is colleted by filtration in a Buchner funnel. The crude precipitate is dissolved in warm (40° C.) acetone/water (2/1, 200 ml). After cooling in an ice-water bath for about two hours the obtained solution is further diluted with more acetone (100 ml) and the white crystalline material formed is colleted by filtration in a Buchner funnel and washed with cold solvent mixture. The filter cake is dried under reduced pressure over silica gel in a desiccator. The S-acetylcysteine derivative can be used directly as an acceptor in the transpeptidation reaction and the S-acetyl group can be removed by either acidic or alkaline hydrolysis.

1.8.6 S-ethylaminocarbonyl-L-cysteine

Cysteine hydrochloride (158 g.) is dissolved in dimethylformamide (1.5 L) and treated at 0° C. with ethyl carbamate (EtNCO, 78.3 g) and allowed to stand for 70 hours at 20° C. Solvent is removed under reduced pressure and the viscous residue triturated with diethyl ether, dissolved in water (2 L) adjusted to pH 6.5 and concentrated by evaporation under reduced pressure to 1.3 L. Crystallization of the concentrate overnight at 0° yielded 131 g. S-ethylaminocarbonyl-L-cysteine. The S-ethylaminocarbonyl group is stable under acidic and neutral conditions, but is readily cleaved by basic reagents; neither desulfuration nor racemization of cysteine have been observed (adapted from Guttmann, S., Synthesis of glutathione and oxytocin by using a new thiol protecting group, *Helvetica Chimica Acta.* 1965, 49, 83-96).

1.9 Synthesis of Glutamic Acid γ-ethyl Ester

Glutamic acid (70 g) was suspended in ethanol (450 mL) and charged into a round bottom flask (1 L) equipped with a magnetic stirrer and thermometer. Sulphuric acid (56 g, 96% (w/v)) was added drop wise into the suspension with strong mixing while maintaining the temperature of the reaction mixture at 27° C. After the addition of sulphuric acid was complete the reaction was kept at room temperature for 2 hours. The mixture was then cooled to 0° C. and to it was added drop wise a solution of potassium hydroxide (64 g in 230 mL of water). The temperature was maintained below 10° C. during the neutralization by cooling the flask. The slurry formed after neutralization was filtered off and the filter cake was washed with a mixture composed of ethanol (79 mL) and water (40 g). The collected solids were dried, yielding potassium sulphate (99 g).

The filtrate was combined with the washings and the mixture was concentrated to a weight of 82 g by rotary evaporation under reduced pressure. To the resulting syrup was added ethanol (105 mL) resulting in spontaneous crystallization. The mixture was allowed to stand overnight at 4° C. and the resulting crystalline suspension was collected by filtration in a Buchner funnel. The filter cake was dried under reduced pressure over silica gel in a dessicator. Upon drying, glutamic acid γ-ethyl ester (67 g, 80% of the theoretical yield), was obtained (melting point 191° C.).

1.10 Preparation of Immobilized γ-Glutamyltranspeptidase

Type 1 bovine kidney γ-GT (100 mg, Sigma-Aldrich) was dissolved in 1 M potassium phosphate buffer at pH 8.5 (6 mL) in a plastic tube (20 mL capacity). Eupergit® C250 L activated immobilizing resin beads (1 g) was added with gentle mixing and the tube incubated undisturbed at room temperature for 3 days. The beads were collected on a sintered glass filter with suction and washed extensively with 0.1 M potassium phosphate buffer at pH 8.5. The immobilized enzyme was stored at 4° C. in the same buffer containing 0.5 g/L of methyl p-hydroxybenzoate.

Suction dried immobilized enzyme (10 mg) was weighed into a Eppendorf tube and is prewarmed in a 37° C. heating block. The γ-GT assay buffer (1 mL) was added and the tube mixed well at 1 min intervals for 5 min. The tube was then centrifuged for a few seconds and the supernatant dispensed into a cuvette containing 1.5 M acetic acid (2 mL). The absorbance at 410 nm was measured in a spectrophotometer and the activity in U/g was calculated as in Example 1.

Example 2

Synthesis of γ-Glutamylcysteine (GGC) with Amide Bonded γ-Glutamyl Donor

Cystine (36 mg, 3 mM) was dissolved with warming in 50 mM sodium phosphate buffer (50 mL) at pH 8.5. An aliquot (10 mL) was dispensed into a test tube containing L-γ-glutamyl-p-nitroanilide (GPNA) (4 mg, 1.5 mM) and pH adjusted to pH 8.5 with 10% NaOH. The tube was incubated at 37° C. and the reaction initiated by the addition of γ-GT (3 mg, 2.2 U/mL). Samples (0.5 mL) were taken at 15, 30 and 90 minute intervals, with the reaction quenched by the addition of an equal volume of 4.5% (w/v) phosphoric acid. Samples were stored at −20° C. prior to HPLC analysis. After 90 min incubation the reaction contained 156 mg/L GGC at yields based on the theoretical maximum of 21% on cystine and 42% on GPNA. The reaction as described above was repeated at 5.5 times the original concentration of substrates (cystine; 16.6 mM, GPNA 8.4 mM) which corresponded to the solubility limits of both GPNA and cystine at pH 8.5 in 100 mM phosphate buffer. The highest concentration of GGC (1.4 g/L) was achieved after 30 min incubation with a yield at 66.5% on GPNA and 34% on cystine It is unlikely that the above reaction would be economically feasible due to the high cost of the substrate L-γ-glutamyl-p-nitroanilide $50.90/g (Sigma). The high cost is related to complex and multiple step synthetic processes required for the manufacture of the substrate.

Example 3

Synthesis of γ-Glutamylcysteine (GGC) with Ester Bonded γ-Glutamyl Donors

The synthesis of GGC with L-glutamine and γ-glutamyl esters as γ-glutamyl donors was performed in aqueous solution. Cystine (50 mg, 20 mM) was added separately to glutamine (14.6 mg, 10 mM) and glutamic acid γ-methyl ester (GME) (16 mg, 10 mM) in test tubes. The contents of each tube was dissolved in 100 mM sodium phosphate buffer (10 mL) and adjusted to pH 8.5 with 2 M NaOH. The reaction was initiated by the addition of γ-GT (3 mg, 2.2 U/mL) and the tubes were incubated at 37° C. with samples taken periodically over 24 hours. The yields of GGC peaked at approximately five hours incubation with 78.4 mg/L of GGC produced with GME at a yield (based on the γ-glutamyl donor) of 3.1% and 1.5 mg/L GGC produced with glutamine at a yield of less than 1%.

Example 4

Inclusion of Water-Miscible Solvents in the Reaction Mixture

The following water miscible organic solvents; acetonitrile, dimethylsulphoxide, dioxan, and dimethylformamide (DMF) were initially tested at a ratio of 50:50 with water for their ability to dissolve cystine. The solvent DMF was identified as the organic co-solvent of choice due to its superior solvating properties. The solubility, however, of the Cys-Merc derivative in the other solvent mixtures is unknown and may be worth exploring.

Synthesis of GGC with GME in the Presence of 50% DMF

Cystine (50 mg, 20 mM) and γ-glutamyl methyl ester (GME, 16 mg, 10 mM) were weighed into a test tube. The contents of the tube was dissolved initially in 100 mM sodium phosphate buffer (5 mL) and an equal volume of dimethylformamide (DMF) (5 mL) added. The reaction was initiated by the addition of γ-GT (3 mg, 2.2 U/mL) and incubated at 37° C. with samples taken periodically over 24 hours. The yield of GGC peaked at approximately 9 hours incubation with 465 mg/L of GGC produced at a yield of 18.6% on GME and 9.3% on cystine. The above reaction was repeated, as the solubility of cystine increases dramatically above pH 9.0 a reaction with the highest possible concentration (saturated solution) of cystine (approximately 30 mM) was performed at pH 9.1. As the phosphate buffer was ineffective at pH 9.1 it was replaced with diethanolamine (DEA) buffer. No significant improvement in the yield of GGC was observed indicating that the solubility of cystine needed to be improved considerably for the reaction to be of practical value.

Example 5

Synthesis of γ-Glutamylcysteine (GGC) with Cysteine Derivatives

As the productivity per unit volume for the proposed enzyme bioprocess is critical for determining if the reaction is to be of practical value, the concentration of the substrates needed to be increased significantly as the limit of solubility of cystine had already been reached at approximately 30 mM (9 g/L). A series of chemical derivatives of cystine that needed to meet the following criteria were evaluated:

Increased solubility in the solvent system

No significant loss in enzyme activity towards the acceptor

The chemical derivative must be easily removed to release free GGC

The formation of a mixed (unsymmetrical) disulphide of cysteine with a soluble thiol such as mercaptoethanol is known. Apart from the increased solubility (~20 g/L) of the Cys-Merc derivative, the major advantage with this type of disulphide linked protecting group is its ease of removal by reductive methods, e.g. alteration of the disulphide-sulphydryl equilibrium with an excess of reducing agent, e.g. mercaptoethanol.

Chemical derivatisation of cystine was attempted to produce a more soluble form of cystine, whilst retaining the enzyme activity. The mixed disulphide of cystine and mercaptoethanol (Cys-Merc) was synthesised as described in Example 1.5.1 and was obtained with a yield of approximately 50% at each of the two steps giving a cumulative yield of 25% based on cystine. The cystine dimethyl ester dihydrochloride (CDME) was synthesised as also described in Example 1.7 at a yield of 90% based on cystine. Both derivatives were determined to have relatively high aqueous solubilities (Cys-Merc~20 g/l, CDME>20 g/L).

Comparison of the Two Cystine Derivatives CDME and Cys-Merc (100 mM) as Acceptors for the Synthesis of GGC in 50:50 Water:DMF at pH 9.0 with GME (100 mM)

Glutamic acid γ-methyl ester (GME, 161 mg, 100 mM) was added separately to cystine dimethyl ester.HCl (CDME) (343 mg, 100 mM) and cysteine-mercaptoethanol mixed disulphide (Cys-Merc) (199 mg, 100 mM) in test tubes. The contents of each tube were initially dissolved in 200 mM diethanolamine (DEA) (5 mL) and an equal volume of DMF (5 mL) added. The pH of the reaction mixtures was adjusted to pH 9.0 with 5 M HCl and the reaction initiated by the addition of γ-GT (12.5 mg, 9 U/mL). The tubes were incubated at 37° C. with samples taken periodically over 21 hours. To remove the methyl ester group, samples taken from the CDME reaction (250 μL) were dispensed into Eppendorf tubes containing 1 M NaOH (250 μL) and incubated at 60° C. for 15 minutes prior to HPLC analysis.

Both cystine derivatives were readily soluble in the solvent mixture (~20 g/L). After 21 hours incubation, the maximum concentration of GGC at 4.7 g/L was attained with the Cys-Merc acceptor substrate with a yield of 18.8% on both substrates (see FIG. 1). After 12 hours incubation the maximum concentration of GGC at 1.6 g/L was attained with the CDME acceptor substrate with a yield of 6.3% on both substrates.

The evaluation of the two soluble derivatives of cystine Cys-Merc and CDME demonstrated that under the same reaction conditions, the final concentration of GGC could be increased by almost 7-fold compared to the previous reaction containing saturated underivatized cystine. The derivative Cys-Merc was a 3-fold more effective γ-glutamyl acceptor than CDME, with the reaction mixture containing 4.7 g/L GGC at a yield of 18.8% on both substrates after 21 hours incubation.

Example 6

Effect of γ-methyl and γ-ethyl Esters of Glutamic Acid at 1:1 and 1:2 Ratios with Cys-Merc on Yields of GGC The effect of variation of the acceptor and donor substrate ratios on GGC yield and ester substituent was investigated.

The derivative Cys-Merc (796 mg, 100 mM) was dissolved in 50:50 DMF/water (40 mL) containing 200 mM DEA. Aliquots (10 mL) were dispensed into four test tubes and the following γ-glutamyl esters substrates dissolved into a tube each; GME (80 mg, 50 mM), GME (161 mg, 100 mM), glutamic acid γ-ethyl ester (GEE) (88 mg, 50 mM), and GEE (175 mg, 100 mM). The pH of the reaction mixtures were adjusted to pH 9.0 with 5 M HCl or 2 M NaOH and the reactions initiated by the addition of γ-GT (7 mg, 5 U/mL). The tubes were incubated at 37° C. with samples taken periodically over 10 hours. A γ-GT enzyme activity assay (Example 1) was performed on the 10 hour sample to determine the stability of the enzyme.

The use of γ-ethyl ester (GEE) of glutamic acid resulted in a 40% increase in the yield of GGC when compared to the γ-methyl ester (GME). A maximum concentration of 7.6 g/L of GGC was attained at a yield of 30.4% on GEE and Cys-Merc in the 100 mM equimolar reaction after 10 hours incubation (see Table 1).

The kinetics of all four reactions followed a similar trend with the γ-ethyl ester yielding approximately 40% more GGC than the γ-methyl ester at both molar ratios, see Table 1. The activity of γ-GT in the 10 hour sample was 0.8 U/mL indicating that there had been a significant loss (84%) in enzyme stability.

When the molar ratio of the acceptor Cys-Merc was doubled, the yield on GEE increased to 48% with a concomitant decrease in yield on Cys-Merc to 24%. Increasing the molar ratio of GEE to Cys-Merc to 2:1 did not increase the yield of GGC on Cys-Merc above 30%, and lowered the yield on GEE to below 15%. The increased reactivity of the γ-ethyl ester towards the aminolysis reaction is presumably due to the stronger electron withdrawing effect of the γ-ethyl group.

TABLE 1

Effect of ester substituent and molar ratios on yields of GGC in 9.5 hour reaction sample

| Substrate | Molar Ratio (Glu:Cys) | GGC (g/L) | Yield GGC on γ-Glu donor (%) | Yield GGC on Cys-Merc (%) |
|---|---|---|---|---|
| γ-methyl ester | 1:2 | 3.8 | 30.7 | 15.3 |
| γ-methyl ester | 1:1 | 4.6 | 18.3 | 18.3 |
| γ-ethyl ester | 1:2 | 6.0 | 48.1 | 24.0 |
| γ-ethyl ester | 1:1 | 7.6 | 30.4 | 30.4 |

Increasing the ratio of acceptor (Cys-Merc) to γ-glutamyl ester increased the yield on GEE, however as cystine is significantly more expensive than the donor (GEE), it was imperative to optimise the yield of GGC on Cys-Merc, thus all subsequent reactions were performed at equimolar ratios.

Example 7

Effect of Reaction pH on Synthesis of GGC and Stability of γ-GT

Glutamic acid γ-methyl ester (85 mg, 100 mM) and Cys-Merc (0.1 g, 100 mM) were weighed into three separate test tubes. The contents of one tube was dissolved in an aliquot of 0.4 M NaH$_2$PO$_4$ (2.5 mL) and an equal volume of DMF (2.5 mL) added. The pH of the mixture was adjusted to pH 7.5 with 2 M NaOH. The contents of the other two tubes were dissolved in an aliquot of 0.4 M DEA (2.5 mL) each, and an equal volume of DMF (2.5 mL) added. The pH of the tubes was adjusted to either pH 8.3 or pH 9.0 with 5 M HCL. The reactions were initiated by the addition of γ-GT (12 mg, 17.2 U/mL) and the tubes incubated at 37° C. with samples taken periodically over 20 hours. Samples (100 μL×2) were taken for HPLC analysis (immediately dispensed into Eppendorf tubes containing 4.5% (w/v) phosphoric acid (100 μL)), and for γ-GT enzyme activity assay both of which were stored at −20° C.

Figure 2A:
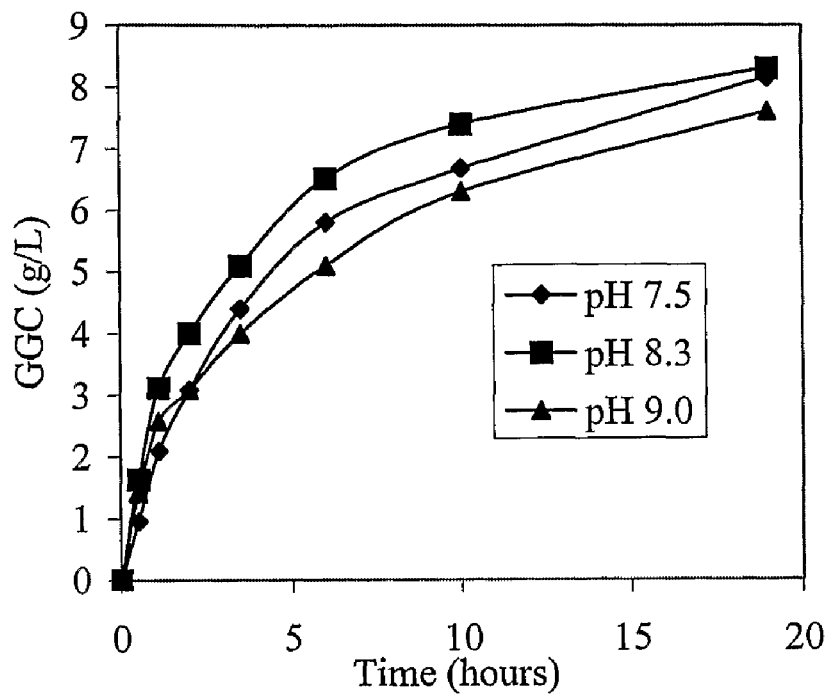
FIGS. 2A and 2B illustrate the effect of pH on reaction kinetics (FIG. 2A) and enzyme stability (FIG. 2B) of γ-GT catalysed GGC synthesis in 50:50 water:DMF with cysteine-mercaptoethanol mixed disulphide (100 mM) and γ-ethyl ester of glutamic acid (GEE, 100 mM) on substrates.

In the reaction run at pH 8.3 after 19 hours incubation the maximum concentration of GGC at 8.3 g/L (see FIG. 2A) was attained with a yield of 33.2% on both substrates. The reactions run at pH 7.5 and 9.0 exhibited a slight decrease in reaction rate and final yields of GGC.

Measurement of enzyme stability under the optimum reaction conditions indicated that significant loss of activity was occurring, with activity decreased to below 10% of the initial activity after 10 hours incubation. As enzymes can be a significant cost in a bioprocess, such as the one proposed, the stability of the enzyme in the reaction mixture needed to be improved considerably if the reaction is to be of practical value.

Figure 2B:
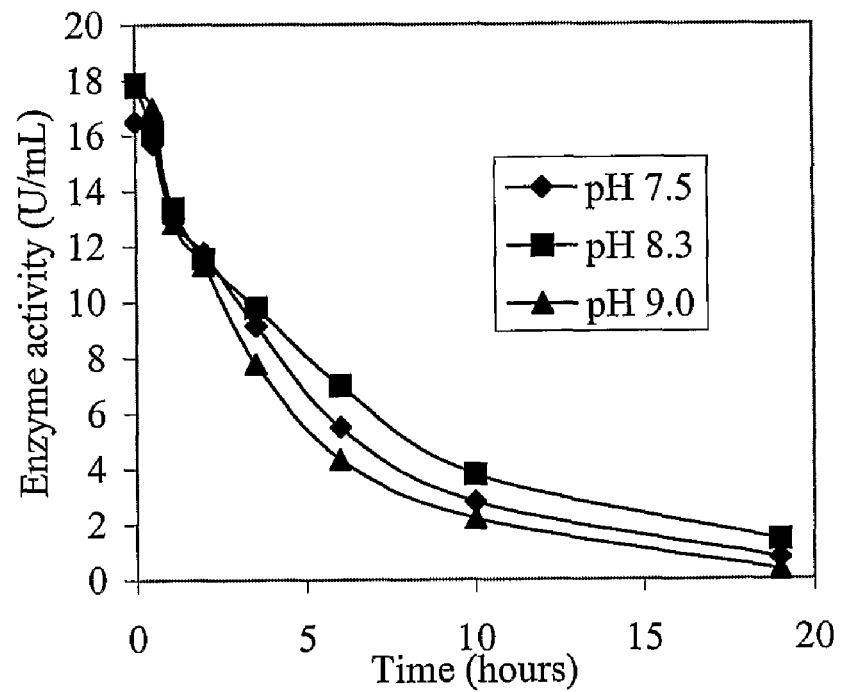

Several options were available to be explored in relation to improving enzyme stability. As the rat kidney γ-GT is irreversibly inactivated above pH 9.4, reaction pH was determined as a possible factor in enzyme stability. However, in the reactions run at pH 7.5, 8.3 and 9.0, no significant difference in enzyme stability was observed in the three pH treatments, with activity decreased to below 30% of the initial activity after 10 hours incubation for all three reaction pH's (FIG. 2B).

Example 8

Synthesis of GGC and Stability with Immobilized Preparation of γ-GT

Suction dried immobilized γ-GT enzyme (200 mg) (Example 1) was weighed into 2 Eppendorf tubes (2 mL capacity). Reaction mixture (1.5 mL) consisting of 50:50 DMF/water solution containing 200 mM DEA and, 100 mM of both Cys-Merc, and GEE at pH 9.0 was added to each tube. The tubes were incubated on a rotating wheel at 10 rpm in a 37° C. incubator. The tubes were centrifuged for a few seconds before sampling to pellet the immobilized enzyme. Samples of supernatant (100 μL) were taken periodically over 30 hours and one of the tubes was replenished with an equal volume of fresh reaction mixture after each sample. A negative control tube containing immobilized enzyme (200 mg) in 200 mM DEA at pH 9.0 (1.5 mL) was also prepared and incubated alongside the reaction tubes. After 30 hours incubation, the used immobilized enzyme from all three tubes was collected on a sintered glass filter and washed extensively with 0.5 M Tris buffer at pH 8.5. A γ-GT activity assay was performed on the used immobilized enzyme as described in Example 1.

In the non-replenished reaction after 30 hours incubation the maximum concentration of GGC at 7.2 g/L was attained with a yield of 28.7% on both substrates. In the replenished reaction after 30 hours incubation the maximum concentration of GGC at 6.8 g/L was attained with a yield of 27.2% on both substrates.

The initial activity of the immobilized γ-GT used in the reaction was 122.3 U/g (see Table 2) which corresponded to a dosage level in the reaction mixture of 16.2 U/mL. After 30 hours incubation 55% of the initial γ-GT activity remained in the non-replenished reaction tube and 48% in the replenished tube. A 10% decrease in the initial γ-GT activity was observed in the negative control tube.

TABLE 2

Stability of immobilized γ-GT after 30 hours incubation in reaction mixture.

| Eupergit C250L, Immobilized γ-GT | Activity (U/g) |
|---|---|
| Initial unused | 122.3 |
| Non-Replenished reaction (50% DMF) | 66.8 |
| Replenished reaction (50% DMF) | 58.7 |
| Negative control (0% DMF) | 110.5 |

The immobilized γ-GT had significantly increased stability with more than 50% of its initial activity retained even after 30 hours incubation (Table 2). Reactions using immobilized γ-GT indicated that there was no significant lowering in both the rates of formation of GGC and final yields of GGC. No significant decrease in yield of GGC was observed in the reaction when the mixture was constantly replenished with fresh reaction mixture. This suggested that the rate of turnover of the immobilized enzyme is satisfactory for a continuous enzyme process, which has several advantages over a batch process, the most noteworthy being the ability to perform reactions at large scale economically by maximizing productivity.

An observation made with the immobilized γ-GT was that the enzyme in the negative control mixture containing no DMF exhibited only a 10% loss in activity over the 30 hour incubation. This indicated that DMF has a significant detrimental effect on enzyme stability.

Example 9

Effect of DMF Concentration on γ-GT Stability

Glutamic acid γ-ethyl ester (43 mg, 100 mM) and Cys-Merc (50 mg, 100 mM) were weighed into four separate test tubes. The contents of a tube each was dissolved in an aliquot of 200 mM DEA (2.5 mL) containing the following concentrations of DMF, 0, 10, 25 and 50%. The pH of the reaction mixtures were adjusted to pH 8.5 with 2 M NaOH or 5 M HCl. The reaction was initiated by the addition of γ-GT (1 mg, 7.2 U/mL). The tubes were incubated at 37° C. with samples taken periodically over 24 hours.

Figure 3:
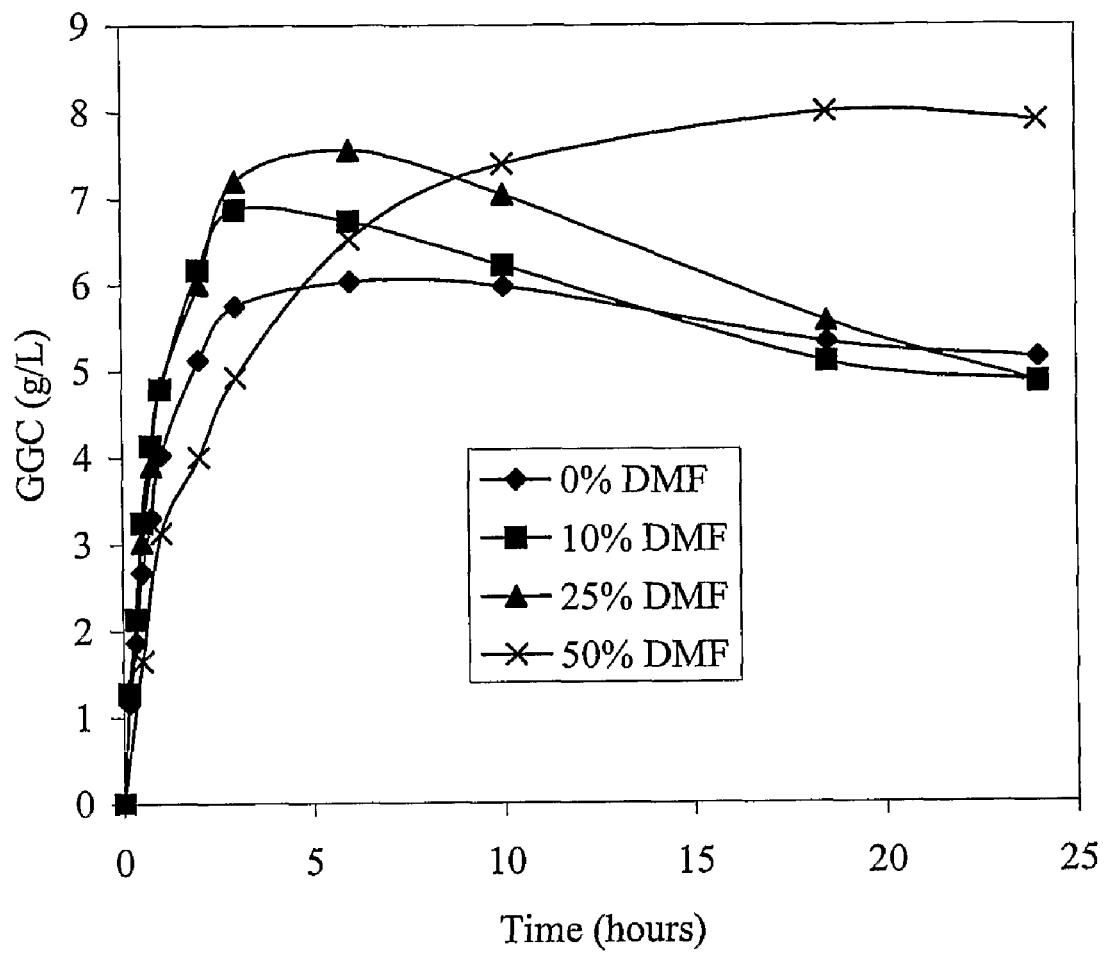
FIG. 3 illustrates the effect of DMF concentration on reaction kinetics of γ-GT catalysed GGC synthesis with Cys-Merc (100 mM) and GEE (100 mM) as substrates.

Unexpected high yields of GGC in the reaction with 100% water were observed with a maximum concentration of GGC at 6.0 g/L (see FIG. 3) attained at a yield of 24% on both substrates after 5 hours incubation. As the DMF concentration was increased the yields of GGC increased with the 10, 25, and 50% DMF treatments yielding 6.9, 7.6 and 8.0 g/L respectively. The kinetics of 0-25% DMF reactions followed a similar pattern, reaching the maximum concentrations of GGC within 5 hours incubation, followed by a decrease in GGC concentration in all reactions to 5 g/L over the subsequent 20 hours. The 50% DMF containing reaction reached the maximum GGC concentration after 18 hours incubation with no further decrease in GGC concentration. Apart from the lowering of water activity, decreasing the hydrolysis reaction, the addition of water miscible solvents also inhibited the amidase activity of γ-GT whilst leaving significant esterase (aminolysis) activity. This was evident in the lack of degradation of the peptide product GGC even after prolonged incubation in the presence of 50% DMF. Secondary hydrolysis was also not observed in the immobilized reactions.

Enzyme activity in 0, 10, and 25% DMF containing reactions was stable over 35 hours incubation, with a nominal loss of 14% activity only after 25 hours in the 25% DMF treatment observed.

Example 10

Enzymatic Synthesis of GGC-Mercaptoethanol Disulphide at pH 8.0 and No Water-Miscible Solvent A flat bottom reactor vessel (500 mL) equipped with a magnetic stirrer, thermometer and a pH probe was charged with R.O. water (150 mL). The vessel was placed in a water bath thermostatted at 37° C. and stirred until the contents reached 37° C. Both Cys-Merc (5.9 g, 0.2 M) and freeze dried cow's milk γ-glutamyltranseptidase (6 Units/mL) were then added and mixed until dissolved. A pH-Stat (Radiometer, PHM 290) was activated to control the pH at pH 8.0 by the addition of sodium hydroxide (2 M). Once the solution had reach pH 8.0 glutamic acid γ-ethyl ester (5.3 g 0.2 M) was added in small lots (~1 g) over 10 minutes. Samples were taken at regular intervals and the production of GGC-Merc and addition of NaOH monitored (See FIG. 4).

After 7 hours incubation the synthesis of GGC-Merc peaked at 92 mM (46% theoretical yield). Due to the acidic nature of GGC-Merc (a dicarboxylic acid) a close coupling of rate of GGC-Merc synthesis and the rate of sodium hydroxide addition to maintain pH 8 was observed.

Example 11

Purification of GGC-Merc

A large difference in the isoelectric point (pI) between the reaction product (GGC-Merc pI=3.0) and the substrates (Cys-Merc, pI=5.3 and GEE pI=5.8) allow purification systems based on ionic charge such as ion exchange chromatography, ion exclusion chromatography and electrodialysis to be readily exploited. Furthermore the ion exchange and electrodialysis methods when performed simultaneously with the enzyme reaction could increase product yield by effectively removing (or trapping) the product as it is formed and thereby driving the equilibrium towards product formation. As an example instead of adding sodium hydroxide to the enzyme reaction described in Example 10 above to neutralize the acidic product GGC-Merc an anion exchange resin in the OH⁻ form could be added to both maintain the pH and selectively remove the reaction product. Similarly the enzyme reaction could be performed in an electrodialysis cell thereby facilitating continuous removal of GGC-Merc Ion Exclusion Chromatography In ion exclusion chromatography the reaction mixture from the enzyme process is adjusted to between pH 5-7 and loaded onto a column of cation exchange resin (sulphonic acid type) in the $Na^+$ form. As GGC-Merc is a stronger acid than the other reaction components it is excluded from entering the resin beads by process called Donnan exclusion thus it elutes in the void volume. The other components (e.g. Cys-Merc mixed disulphide) are either uncharged or have a slight positive charge and are able to diffuse inside the resin beads and thus elute later. The major advantage of this technique is that pure water is used as the mobile phase and no salt or pH gradient is necessary to elute the products. As described by (Eisenbraun, "Separation of amino acids by ion exclusion", 1962, U.S. Pat. No. 3,045,026) for the separation of L-glutamic acid from protein hydrolysates it is also possible to run this type of separation in a continuous mode. By timing the alternative feeding of water and reaction mixture onto the column a new batch of reaction mixture can be loaded onto the column before the first has eluted (see FIG. 5). Chromatography conditions can also be manipulated to separate salt from GGC-Merc by altering the initial pH.

Figure 6:
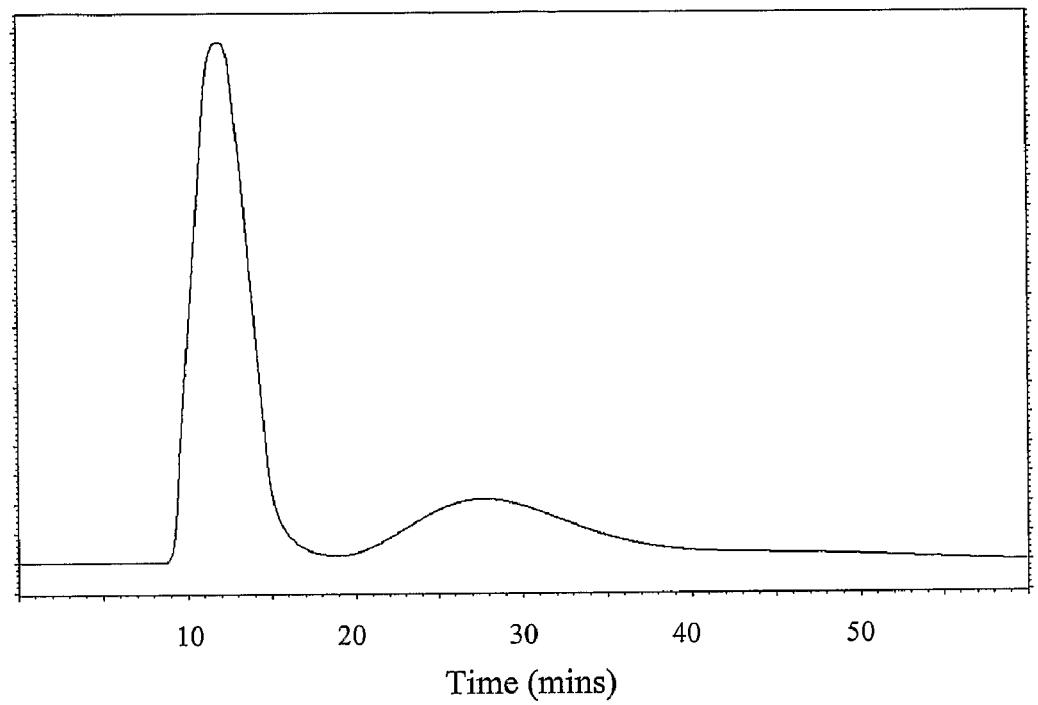
FIG. 6 Provides a preparative ion exclusion chromatography elution profile for an enzyme reaction mixture prepared by a process according to the invention comprising γ-GGC-mercaptoethanol disulphide (first elution peak) and reactants and by-products (subsequent peaks).

Experimentally, a column (3.5 cm diameter×30 cm height) packed with sulphonic acid cation exchange resin (Dowex 50WX4, 100-200 mesh size) in the sodium form was prepared. The column was equilibrated at room temperature with a mobile phase of R.O. water (15 mL/min). Each cycle of separation consisted of an injection onto the column of enzyme reaction mixture prepared as in Example 10 (10 mL, adjusted to pH 5.0). The absorbance at 250 nm of the effluent was monitored by an online UV-Vis HPLC detector. The concentration of disulphides was proportional to the absorbance at 250 nm and fractions of effluent were collected by the use of a fraction collector. The fractions corresponding to the peaks (see FIG. 6) were collected between 9 to 40 min and analysed by HPLC; 9-13 min, GGC-Merc 1.6 mM, 14-16 min 5-oxoproline 1.5 mM, 20-33 min Cys-Merc 0.5 mM. To increase the number of separations in a given period the subsequent aliquots of enzyme reaction mixture could be increased by injection before the last peak of the previous injection had eluted.

Example 12

Electrochemical Reduction of GGC-Merc

Figure 8:
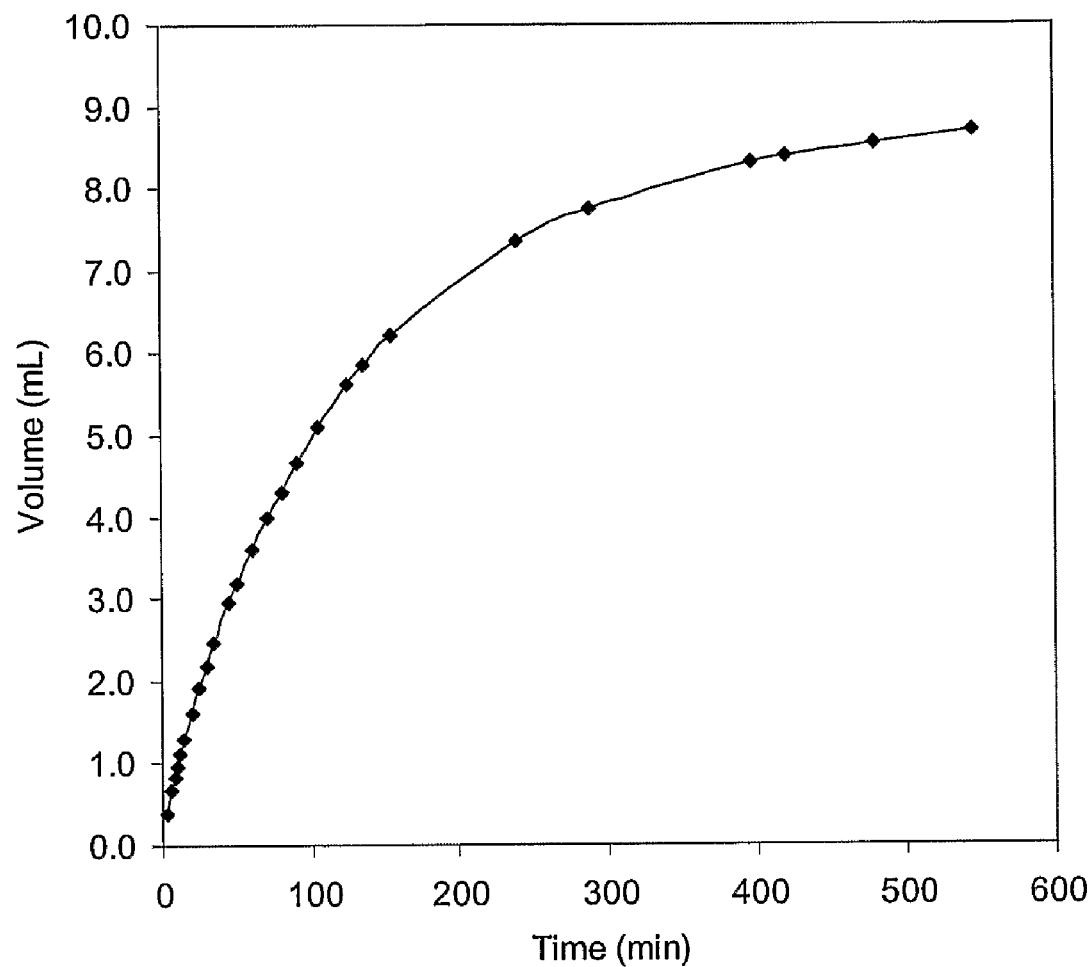
FIG. 8 is a graph of sodium hydroxide addition to the catholyte reservoir during electrochemical reduction of GGC-mercaptoethanol disulphide as described in Example 12.

A Parallel plate filter press flow cell (see FIG. 7) with a geometrical cathode area of 50 cm$^2$ and electrolyte channels 10 cm in the direction of electrolyte flow and 0.5 cm wide (in the direction of current flow) was assembled as previously described (Ralph, et al., Evaluation of a reactor model and cathode materials for batch electrolysis of L-cystine hydrochloride, *Journal of Electroanalytical Chemistry*, 1999, 462, 97-110). A Nafion® 117 cation exchange membrane was used to divide the catholyte and anolyte compartments. The cell housing, end plate and cell frames were constructed from polypropylene. The complete assembly was sealed with neoprene gaskets and the screw press tightened. An electrolyte flow loop provided batch recycle operation for both catholyte and anolyte. Batch electrolyses were performed with a lead cathode and a catholyte (200 mL) containing up to 0.2 M GGC-Merc disulphide, maintained at a constant temperature and pH of 25° C. and pH 7 respectively in the reservoir. The anode was platinised-titanium and the anolyte (200 mL) was 2 M sulphuric acid. Prior to electrolysis, both electrodes were wet polished with 1200 grade silicone carbide paper. The catholyte and anolyte flow rates were set at 20 mL/min using a peristaltic pump and a constant current of 1 A at 3 V was applied to the cell. Periodically samples were removed from the anolyte reservoir for HPLC analysis and the volume of 1 M sodium hydroxide added by the pH-Stat to maintain pH 7 was recorded. Electrochemical reduction was performed on both untreated enzyme reaction mixture and on pooled fractions of purified GGC-Merc. The complete reduction of all disulphide bonds was achieved within several hour of electrolysis for both mixtures. Due to the acidic nature of the free thiol group a close coupling of rate of disulphide reduction and the rate of sodium hydroxide addition to maintain pH 7 in the catholyte was observed (See FIG. 8). The GGC content of the catholyte prepared from untreated/unseparated enzyme reaction mixture can be subjected to ion exclusion chromatography, carried out similarly to the method described in Example 11, with a similar degree of effectiveness, however special precautions are required to prevent re-oxidation of the GGC.

Example 13

Separation of Mercaptoethanol from GGC

2-Mercaptoethanol generated by the electrochemical reduction as described in Example 12 was effectively removed by partitioning into organic solvent. Several batches of catholyte from the electrochemical reduction (Example 12) were extracted three times with 50% volumes of either 1-butanol, ethyl acetate, butyl acetate or 2-ethyl-1-hexanol. To prevent re-oxidation of the thiols all operations were conducted under a nitrogen atmosphere. The 2-mercaptoethanol was effectively reduced to less than 5% of the original concentration in the aqueous phase by all four solvents tested.

After the extraction of 2-mercapethanol from the reduced pooled fractions of GGC-Merc, pure GGC was obtained as a cream white powder by freeze drying. Purity as determined by HPLC: GGC 98%, (cysteine 1%, mercaptoethanol undetectable).

Example 14

Commercial Bioprocess for the Production of GGC

Figure 9:
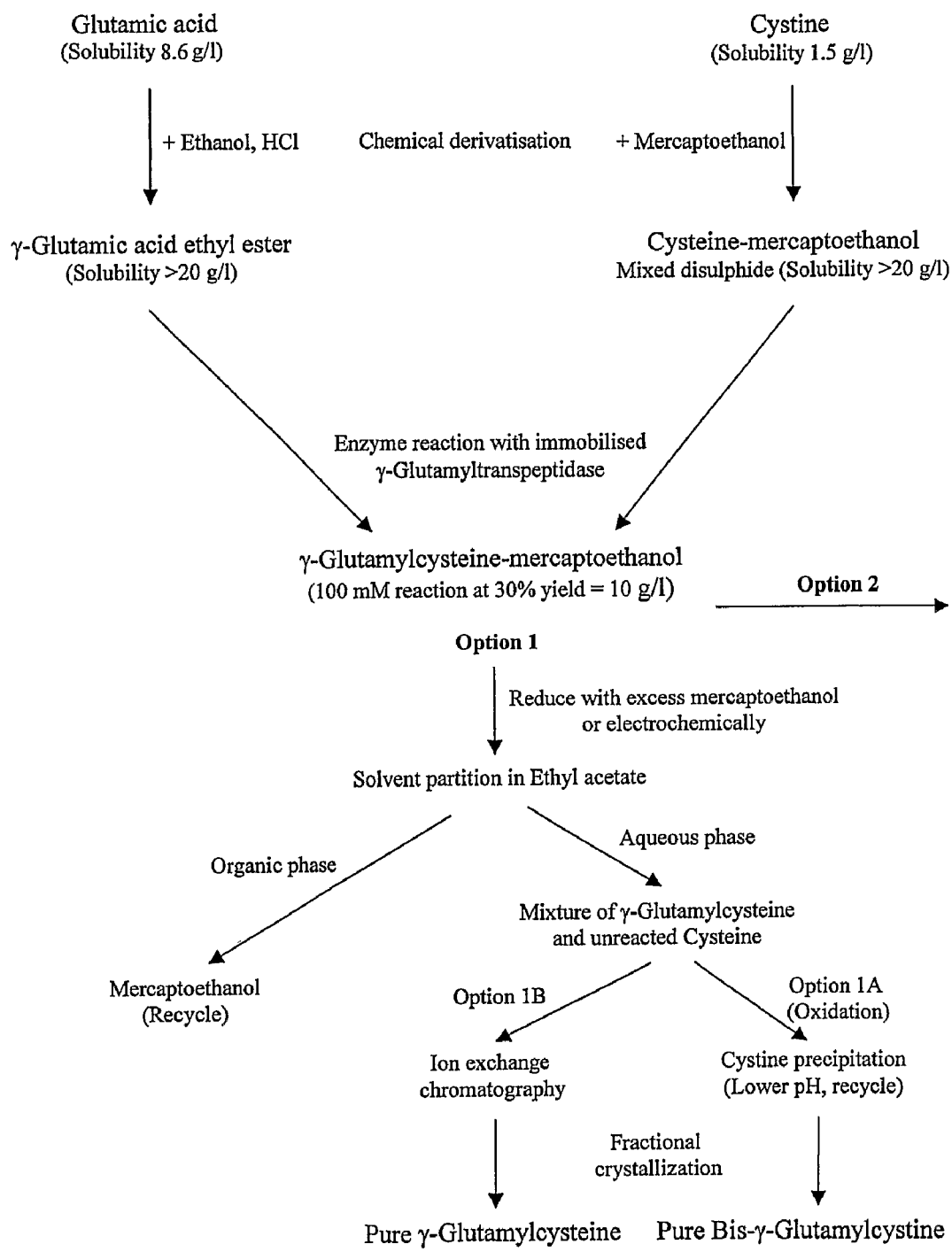
FIG. 9 is a flow diagram for a commercial bioprocess of the invention for the production of γ-GGC.

From the outcomes of these studies, a commercial bioprocess for the production of GGC using γ-GT, as shown in FIG. 9, may be developed. The first two steps consist of chemical derivatisation of the two amino acid substrates. The subsequent γ-GT catalysed synthesis can be performed with immobilized enzyme in either a batch process or, more advantageously, in a continuous process. Bovine milk has been identified as an excellent source of γ-GT, containing up to 5 U/mL. Suitable methods for purification of γ-GT from bovine milk, suitable for industrial production, have been previously described in Example 1.3. Ideally, immobilized γ-GT is packed into a column and fresh substrate is pumped continuously in one end and reaction mixture containing GGC withdrawn from the other end. If 50% DMF is not used as a co-solvent, then the reaction requires monitoring to determine the kinetic optimum (or residence time in a continuous process) for harvesting the GGC before any significant secondary hydrolysis has occurred. Alternatively, the reaction can be carried out at a pH of about 8.0, which has found to result in significantly less amidase activity of the γ-GT and less hydrolysis of the γ-GGC derivative product.

Several options exist for the removal of unreacted substrates and for the purification of GGC or derivative thereof (Such as GGC-Merc) from the reaction mixture. Preferred methods for purification of GGC, or GGC-Merc (and subsequent reduction to GGC) are as described in Examples 11 to 12 above.

Example 13 describes purification of GGC from a mixture comprising GGC and 2-mercaptoethanol, with subsequent freeze-drying. However, it is not expected that freeze drying would be an economic option at industrial scale. Removal of water by conventional evaporation at temperatures above 40° C. results in degradation of the product. However, a process of concentration by nanofiltration is expected to be most suitable at industrial scale as it is both low temperature and a cost effective method for water removal. The effectiveness of nanofiltration for the concentration of amino acids and peptides is well established (Martin-Orue, C. et al., Nanofiltration of amino acid and peptide solutions: mechanisms of separation, *Journal of Membrane Science*, 1998, 142, 225-33) and recently the use of nanofiltration for the separation of glutathione was demonstrated (Gotoh, K. et al., Separation of glutathione and its related amino acids by nanofiltration, *Biochemical Engineering Journal*, 2004, 19, 165-70). After the removal of the majority of water by nanofiltration and a pH adjustment to the pH of the isoelectric point (GGC=pH 2.8) the addition of an antisolvent such as ethanol or acetone can be added to initiate spontaneous crystallization. The final product can be collected by filtration and dried under reduced pressure.

Figure 10:
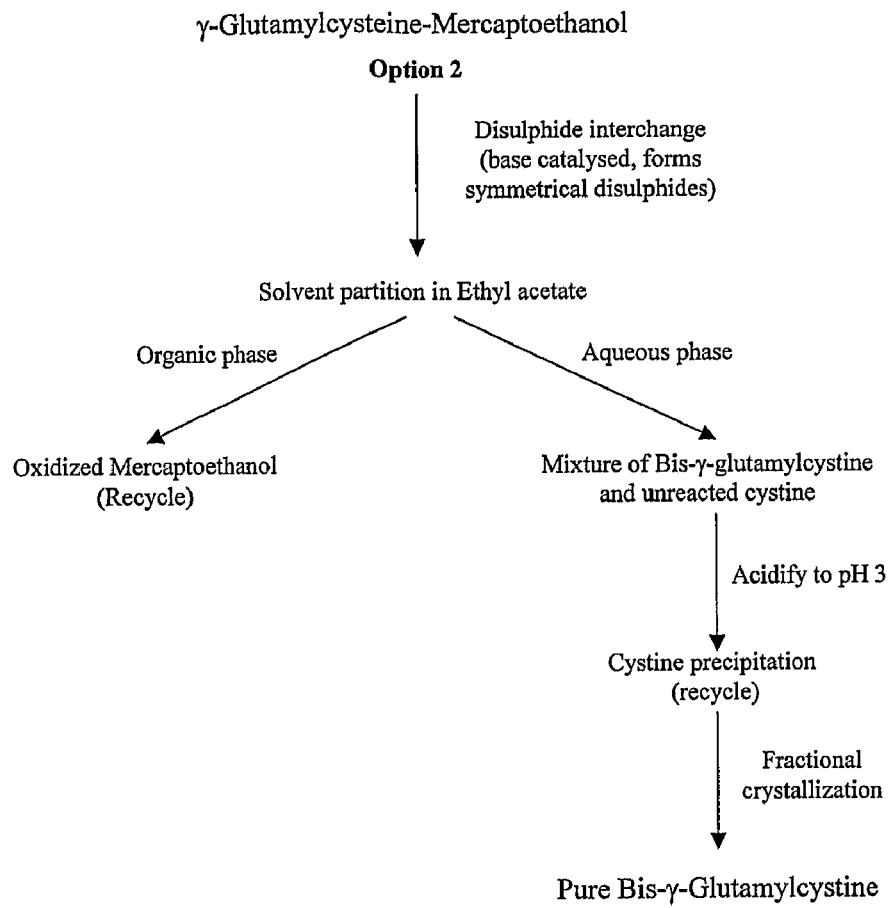
FIG. 10 is a flow diagram for a second option for obtaining γ-GGC from γ-glutamylcysteine-mercaptoethanol by a process as illustrated in FIG. 4.

Two other possible industrially applicable options for purification of GGC produced by a method of the invention are described below and are illustrated in FIGS. 9 and 10. The insolubility of cystine, which was a drawback during the synthesis of GGC, can be used to advantage in the subsequent purification of GGC.

Purification Option 1

One option is to initially reduce all disulphide bonds in the reaction mixture by either addition of excess mercaptoethanol or by electrochemical reduction:

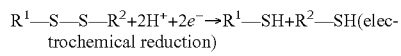

$R^1$—S—S—$R^2$+2H$^+$+2$e^-$→$R^1$—SH+$R^2$—SH(electrochemical reduction)

Solvent extraction with ethyl acetate can be used to selectively partition both reduced and oxidized mercaptoethanol into the organic phase. The aqueous phase containing a mixture of GGC, cysteine and glutamate can either be purified by ion exchange chromatography (Option 1A) to yield pure GGC (reduced). For example, the mixture can be purified by ion exchange chromatography on a Dowex I formate column. The column is initially washed with a linear gradient established between equal volumes of water and 0.4M formic acid. The eluted fractions containing GGC can be combined and then freeze-dried. The other alternative (Option 1B) is to re-oxidize the thiols in the mixture by prolonged exposure to air to form cystine, which will precipitate on lowering to pH 3 (cystine solubility at pH 3, 0.1 g/L). After removal of solids the solution can be concentrated by evaporation and pure bis-γ-glutamylcystine can be fractionally crystallised from the remaining, free acid form of glutamic acid, which is soluble at only 8.6 g/L.

Purification Option 2

The second option is to induce a disulphide interchange reaction:

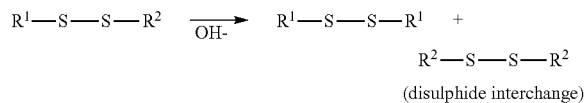

In the reaction scheme proposed all of the mixed (unsymmetrical) disulphides (Cys-Merc and GGC-Merc) in the reaction mixture are converted to their symmetrical disulphides (cystine, Bis-γ-glutamylcystine and mercaptoethanol disulphide) by treatment with dilute NaOH (the base should also saponify any GEE to ethanol and glutamate). The resulting mercaptoethanol disulphide is removed by solvent partition in ethyl acetate. Lowering the pH of the aqueous phase to pH 3 should result in precipitation of the cystine and the purification as described for option 1A can be followed to yield pure bis-γ-glutamylcystine.

Final Form of GGC Product

The final form of GGC, whether it be in the reduced state as γ-glutamylcysteine or in the disulphide form as bis-γ-glutamylcystine, is dependent on the final application of the dipeptide. Preliminary studies on the utilization of GGC in mice indicated that administration of both the reduced and disulphide forms of GGC significantly increase glutathione levels. The oxidised form bis-γ-glutamylcystine is more likely to be suitable for application as a nutraceutical supplement as no special precautions to prevent the oxidation of the sulphydryl, would be required, whereas application in the treatment of poisoning or as an antioxidant in food or cosmetics would require the reducing power of the sulphydryl of γ-glutamylcysteine. Whatever the desired form, both are relatively easily interconverted by reduction which can be achieved either chemically (Jocelyn, P. C., Chemical reduction of disulfides. *Methods in Enzymology*, 1987. 143: p. 246-56), electrochemically (Genders, J. D., N. L. Weinberg, and D. J. Mazur, High yield methods for electrochemical preparation of cysteine and analogues. 1988, U.S. Pat. No. 5,106,463. The Electrosynthesis Company, Inc.) or oxidized to the disulphide form simply by exposing a solution to air (oxygen) with a trace amount of copper or iron salt added to catalyse the reaction.

The GGC may also be provided as a salt:

With Cations: Na, K, Ca, Mg, salt dimers with basic amino acids e.g. leucine, arginine, and salts with polyamines such as chitosan; or With anions: HCl, methane sulphonic acid, acetate, and polycations such as Carboxymethylcellulose.

It will be appreciated that, although specific embodiments of the invention have been described herein for the purpose of illustration, various modifications may be made without deviating from the spirit and scope of the invention as defined in the following claims.

The invention claimed is:

1. A process for preparing a γ-glutamyl cysteine derivative comprising an α,γ-amide linkage between a cysteine moiety and a glutamic acid moiety, comprising reacting a cysteine derivative comprising a cysteine moiety, a γ-glutamyl donor comprising a γ-glutamyl moiety and an enzyme capable of transferring the γ-glutamyl moiety of the γ-glutamyl donor to the cysteine moiety of the cysteine derivative in a reaction environment that promotes transfer of the γ-glutamyl moiety to the cysteine derivative, wherein the cysteine derivative is selected from the group consisting of:

a mixed disulphide of cysteine and a low molecular weight water-soluble thiol;

S-acetylcysteine;

an S-acetamidoalkyl derivative of cysteine;

an S-alkoxycarbonylsulphenyl derivative of cysteine;

S-sulphocysteine;

S-ethylaminocarbonylcysteiene;

and an alkyl ester of cystine, wherein the γ-glutamyl cysteine derivative is obtained.

2. The process of claim 1, wherein said enzyme has γ-glutamyl esterase or γ-glutamyl amidase activity.

3. The process of claim 2, wherein said enzyme is a γ-glutamyltranspeptidase.

4. The process of claim 1, wherein said γ-glutamyl donor is a γ-ester or a γ-amide of glutamic acid.

5. The process of claim 4, wherein said γ-glutamyl donor is a γ-glutamyl-ester.

6. The process of claim 4, wherein said γ-glutamyl donor is a γ-alkyl-, α,γ-dialkyl-, γ-p-chlorophenyl-, or γ-cyanomethyl-ester of glutamic acid.

7. The process of claim 6, wherein said γ-glutamyl donor is γ-methyl, γ-ethyl, α,γ-dimethyl, α,γ-diethyl-ester of glutamic acid.

8. The process of claim 7, wherein said γ-glutamyl donor is γ-glutamyl-ethyl ester.

9. The process of claim 1, wherein the cysteine derivative is water-soluble.

10. The process of claim 1, wherein the cysteine derivative is selected from the group consisting of:
a mixed disulphide of cysteine and a low molecular weight water-soluble thiol;
S-acetylcysteine;
S-acetamidomethylcysteine;
S-methoxycarbonylsulphenylcysteine:
S-sulphocysteine;
cystine dimethyl ester; and
cystine monomethyl ester.

11. The process of claim 10, wherein the mixed disulphide of cysteine and a low molecular weight water-soluble thiol is cysteine-mercaptoethanol mixed disulphide.

12. The process of claim 1, wherein the reaction environment is aqueous.

13. The process of claim 12, wherein a water-miscible solvent is included in the reaction environment.

14. The process of claim 13, wherein the reaction environment comprises from about 30% to about 60% v/v water-miscible solvent.

15. The process of claim 14, wherein the water-miscible solvent comprises dimethylformamide.

16. The process of claim 15, wherein the water-miscible solvent is dimethylformamide.

17. The process of claim 16, wherein the reaction environment comprises about 50% v/v dimethylformamide.

18. The process of claim 1, wherein the enzyme is a bovine γ-glutamyltranspeptidase.

19. The process of claim 18, wherein the enzyme is obtained from bovine kidney or bovine milk.

20. The process of claim 18, wherein the reaction environment is maintained at a pH of from about 8.0 to about 9.0.

21. The process of claim 1, wherein the enzyme is immobilized on a stationary phase.

22. The process of claim 21, wherein the enzyme is immobilized on a resin.

23. The process of claim 1 which is a batch-wise process.

24. The process of claim 1 which is a continuous process.

25. The process of claim 24, wherein the γ-glutamyl donor and the cysteine derivative are continuously fed into an inlet of a reactor having an outlet wherein the enzyme is immobilized and eluate comprising the γ-glutamyl cysteine derivative is collected continuously from the outlet.

26. The process of claim 1, γ-glutamyl donor is a γ-glutamyl ester and the enzyme is a γ-glutamyltranspeptidase.

27. The process of claim 26, wherein the γ-glutamyl ester is selected from γ-methyl-, γ-ethyl-, α,γ-dimethyl-, and α,γ-diethyl-esters of glutamic acid; and
the cysteine derivative is a mixed disulphide of cysteine a low molecular weight water-soluble thiol.

28. The process according to claim 27, wherein the low molecular weight water.

29. The process of claim 26, wherein:
the γ-glutamyl ester is γ-glutamyl-ethyl ester; and
the cysteine derivative is cysteine-mercapthoethanol mixed disulphide.

30. The process of claim 1, further comprising purifying the γ-glutamylcysteine derivative by electrodialysis or by ion exclusion chromatography.

31. The process of claim 1, wherein the γ-glutamylcysteine derivative is γ-glutamylcysteine-mercaptoethanol disulphide.

32. The process of claim 1, further comprising cleaving the γ-glutamylcysteine derivative to obtain γ-glutamylcysteine.

33. The process of claim 32, wherein the cleavage is by electrochemical reduction.

34. The process of claim 32, further comprising isolating the γ-glutamylcysteine and optionally purifying the isolated γ-glutamylcysteine in reduced or oxidized form.

* * * * *